(12) United States Patent
Huang et al.

(10) Patent No.: US 11,568,584 B2
(45) Date of Patent: Jan. 31, 2023

(54) SYSTEMS AND METHODS FOR MAGNETIC RESONANCE IMAGING

(71) Applicant: SHANGHAI UNITED IMAGING INTELLIGENCE CO., LTD., Shanghai (CN)

(72) Inventors: Xiaoqian Huang, Shanghai (CN); Shu Liao, Shanghai (CN)

(73) Assignee: SHANGHAI UNITED IMAGING INTELLIGENCE CO., LTD., Shanghai (CN)

(*) Notice: Subject to any disclaimer, the term of this patent is extended or adjusted under 35 U.S.C. 154(b) by 205 days.

(21) Appl. No.: 17/002,817

(22) Filed: Aug. 26, 2020

(65) Prior Publication Data
US 2021/0065413 A1 Mar. 4, 2021

(30) Foreign Application Priority Data

Aug. 26, 2019 (CN) .......................... 201910789671.3
Oct. 31, 2019 (CN) .......................... 201911053237.5

(51) Int. Cl.
*G06T 11/00* (2006.01)
*G16H 30/40* (2018.01)
(Continued)

(52) U.S. Cl.
CPC ............ *G06T 11/006* (2013.01); *A61B 5/055* (2013.01); *A61B 5/7267* (2013.01); *G16H 30/40* (2018.01);
(Continued)

(58) Field of Classification Search
CPC ............... G06T 11/006; G06T 2210/41; G06T 2210/424; G06T 7/0012; G06T 2207/20084; G06T 2207/20081; G16H 30/40; A61B 5/055; A61B 5/7267; G06N 3/08

See application file for complete search history.

(56) References Cited

U.S. PATENT DOCUMENTS 9,297,873 B2* 3/2016 Block ................ G01R 33/5611
2017/0053402 A1* 2/2017 Migukin .............. G01R 33/561
(Continued)

OTHER PUBLICATIONS

B. Gözcü et al., "Learning-Based Compressive MRI," in IEEE Transactions on Medical Imaging, vol. 37, No. 6, pp. 1394-1406, Jun. 2018, doi: 10.1109/TMI.2018.2832540. (Year: 2018).*

(Continued)

*Primary Examiner* — Vu Le
*Assistant Examiner* — Julius Chai
(74) *Attorney, Agent, or Firm* — Metis IP LLC

(57) ABSTRACT

A system for Magnetic Resonance Imaging (MRI) is provided. The system may obtain at least one training sample each of which includes full MRI data. The system may also obtain a preliminary subsampling model and a preliminary MRI reconstruction model. The system may further generate a subsampling model corresponding to an MRI reconstruction model by jointly training the preliminary subsampling model and the preliminary MRI reconstruction model using the at least one training sample. The subsampling model may be the trained preliminary subsampling model, and the MRI reconstruction model may be at least a portion of the trained preliminary MRI reconstruction model.

20 Claims, 14 Drawing Sheets

(51) Int. Cl.
*A61B 5/055* (2006.01)
*A61B 5/00* (2006.01)
*G06N 3/08* (2006.01)

(52) U.S. Cl.
CPC ............ *G06N 3/08* (2013.01); *G06T 2210/41* (2013.01); *G06T 2211/424* (2013.01)

(56) References Cited

U.S. PATENT DOCUMENTS

| | | | |
|---|---|---|---|
| 2017/0061620 A1* | 3/2017 | Park | G06T 5/50 |
| 2019/0059780 A1* | 2/2019 | Lee | A61B 5/7207 |
| 2019/0122398 A1* | 4/2019 | Huang | G06T 9/00 |
| 2019/0351261 A1* | 11/2019 | Levy | G01R 33/561 |
| 2020/0072933 A1* | 3/2020 | Ye | G01R 33/56554 |
| 2021/0035337 A1* | 2/2021 | Kim | G16H 30/40 |
| 2021/0224952 A1* | 7/2021 | Pawar | G06T 3/4046 |
| 2022/0075017 A1* | 3/2022 | Sabuncu | G06N 3/0454 |
| 2022/0130017 A1* | 4/2022 | Zhang | G01R 33/5608 |

OTHER PUBLICATIONS

Bahadir, Cagla Deniz, Adrian V. Dalca, and Mert R. Sabuncu. "Learning-based optimization of the under-sampling pattern in MRI." International Conference on Information Processing in Medical Imaging. Springer, Cham, 2019. (Year: 2019).*

Hyun, Chang Min, et al. "Deep learning for undersampled MRI reconstruction." Physics in Medicine & Biology 63.13 (2018): 135007. (Year: 2018).*

D. Lee, J. Yoo, S. Tak and J. C. Ye, "Deep Residual Learning for Accelerated MRI Using Magnitude and Phase Networks," in IEEE Transactions on Biomedical Engineering, vol. 65, No. 9, pp. 1985-1995, Sep. 2018, doi: 10.1109/TBME.2018.2821699. (Year: 2018).*

Mark A. Griswold et al., Generalized Autocalibrating Partially Parallel Acquisitions (GRAPPA), Magnetic Resonance in Medicine, 47(6): 1202-1210, 2002.

Klaas P. Pruessmann et al., SENSE: Sensitivity Encoding for Fast MRI, Magnetic Resonance in Medicine, 42(5) 952-962, 1999.

Ricardo Otazo et al., Combination of Compressed Sensing and Parallel Imaging for Highly Accelerated First-Pass Cardiac Perfusion MRI, Magnetic Resonance in Medicine, 64(3): 767-776, 2010.

Bo Zhu et al., Image Reconstruction by Domain Transform Manifold Learning, Nature, 555(7697), 2018, 18 pages.

Kai Xuan et al., Learning MRI k-Space Subsampling Pattern Using Progressive Weight Pruning, Medical Image Computing and Computer Assisted Intervention, 12262: 178-187, 2020.

* cited by examiner

Si: an intermediate subsampling model of an $i^{th}$ iteration
Ri: an intermediate MRI reconstruction model of the $i^{th}$ iteration
Mi: a subsampling MRI image of a training sample generated in the $i^{th}$ iteration
Mi': a predicted full MRI image of a training sample generated in the $i^{th}$ iteration $s_i$: an intermediate subsampling model of an $i^{th}$ iteration
$r_i$: an intermediate MRI reconstruction model of the $i^{th}$ iteration
$m_i$: a subsampling MRI image of a second training sample generated in the $i^{th}$ iteration
$m_i'$: a predicted full MRI image of a second training sample generated in the $i^{th}$ iteration

1400

```
┌─────────────────────────────────────────────────┐
│ Obtaining target subsampled k-space data of a   │
│ target subject by performing an MRI scan on the │ ~ 1410
│ target subject according to a subsampling model │
└─────────────────────────────────────────────────┘
                        │
                        ▼
┌─────────────────────────────────────────────────┐
│ Generating a target subsampled MRI image of the │ ~ 1420
│ target subject based on the target subsampled   │
│ k-space data                                    │
└─────────────────────────────────────────────────┘
                        │
                        ▼
┌─────────────────────────────────────────────────┐
│ Generating a target full MRI image of the target│
│ subject by processing the target subsampled MRI │ ~ 1430
│ image using an MRI reconstruction model         │
└─────────────────────────────────────────────────┘
```

Fig. 14

SYSTEMS AND METHODS FOR MAGNETIC RESONANCE IMAGING

CROSS-REFERENCE TO RELATED APPLICATIONS

This application claims priority to Chinese Patent Application No. 201910789671.3, filed on Aug. 26, 2019, and Chinese Patent Application No. 201911053237.5, filed on Oct. 31, 2019, the contents of each of which are hereby incorporated by reference.

TECHNICAL FIELD

The disclosure generally relates to Magnetic Resonance Imaging (MRI), and more particularly, relates to systems and methods for generating a subsampling model and an MRI reconstruction model.

BACKGROUND

With the development of medical technologies, various medical imaging devices have emerged to acquire medical images of a subject (e.g., a patient). Among these medical imaging devices, an MRI device, which causes little or no ionizing radiation damage to the subject and is capable of acquiring multi-dimensional information (e.g., T1 information, T2 information, etc.) of the subject, has become an important tool for medical diagnosis and/or treatment.

SUMMARY

An aspect of the present disclosure relates to a system for Magnetic Resonance Imaging (MRI). The system may include at least one storage device including a set of instructions and at least one processor in communication with the at least one storage device. When executing the set of instructions, the at least one processor may be directed to perform operations. The operations may include obtaining at least one training sample each of which includes full MRI data. The operations may include obtaining a preliminary subsampling model and a preliminary MRI reconstruction model. The operations may further include generating a subsampling model corresponding to an MRI reconstruction model by jointly training the preliminary subsampling model and the preliminary MRI reconstruction model using the at least one training sample. The subsampling model may be the trained preliminary subsampling model, and the MRI reconstruction model may be at least a portion of the trained preliminary MRI reconstruction model.

In some embodiments, the jointly training the preliminary subsampling model and the preliminary MRI reconstruction model may include an iterative operation including one or more iterations. The at least one iteration of the one or more iterations may include obtaining, based on the preliminary subsampling model and the preliminary MRI reconstruction model, an intermediate subsampling model and an intermediate MRI reconstruction model. The at least one iteration of the one or more iterations may include determining whether the intermediate subsampling model satisfies a termination condition. In response to determining that the intermediate subsampling model does not satisfy the termination condition, the at least one iteration of the one or more iterations may further include updating, based on the intermediate MRI reconstruction model and at least a portion of the at least one training sample, the intermediate subsampling model.

In some embodiments, the at least one iteration may be the first iteration among the one or more iterations. The intermediate subsampling model may be the preliminary subsampling model and the intermediate MRI reconstruction model may be the preliminary MRI reconstruction model.

In some embodiments, the one or more iterations may include a plurality of iterations. The at least one iteration may be subsequent to the first iteration among the one or more iterations. The intermediate subsampling model may be an updated intermediate subsampling model generated in a previous iteration, and the intermediate MRI reconstruction model may be an updated intermediate subsampling model generated in the previous iteration or the preliminary MRI reconstruction model.

In some embodiments, for the at least one iteration, the determining whether the intermediate subsampling model satisfies a termination condition may include, for each of the at least a portion of the at least one training sample, generating a subsampled MRI image based on the intermediate subsampling model and the full MRI data of the training sample. The determining whether the intermediate subsampling model satisfies a termination condition may include, for each of the at least a portion of the at least one training sample, generating a predicted full MRI image based on the subsampled MRI image and the intermediate MRI reconstruction model. The determining whether the intermediate subsampling model satisfies a termination condition may also include, for each of the at least a portion of the at least one training sample, generating a determination result of whether the predicted full MRI image satisfies a preset condition. The determining whether the intermediate subsampling model satisfies a termination condition may further include determining whether the intermediate subsampling model satisfies the termination condition based on the determination result of each of the at least a portion of the at least one training sample.

In some embodiments, for each of the at least a portion of the at least one training sample, the generating a determination result of whether the predicted full MRI image satisfies a preset condition may include obtaining a full MRI image based on the full MRI data of the training sample. The generating a determination result of whether the predicted full MRI image satisfies a preset condition may include determining a difference between the full MRI image and the predicted full MRI image of the training sample. The generating a determination result of whether the predicted full MRI image satisfies a preset condition may further include determining whether the predicted full MRI image satisfies the preset condition by determining whether the difference exceeds a threshold difference.

In some embodiments, in response to determining that the intermediate subsampling model does not satisfy the termination condition, the updating the intermediate subsampling model based on the intermediate MRI reconstruction model and at least a portion of the at least one training sample may include, for each of the at least a portion of the at least one training sample, generating predicted full k-space data based on the predicted full MRI image of the training sample. The updating the intermediate subsampling model based on the intermediate MRI reconstruction model and at least a portion of the at least one training sample may include, for each of the at least a portion of the at least one training sample, obtaining full k-space data based on the full MRI data of the training sample. The updating the intermediate subsampling model based on the intermediate MRI reconstruction model and at least a portion of the at least one training sample may include, for each of the at least a portion of the at least one training sample, generating a comparison result between the predicted full k-space data and the full k-space data of the training sample. The updating the intermediate subsampling model based on the intermediate MRI reconstruction model and at least a portion of the at least one training sample may include updating the intermediate subsampling model based on the comparison result of each of the at least a portion of the at least one training sample.

In some embodiments, the intermediate subsampling model may define a plurality of first k-space lines among a plurality of k-space lines. For each of the at least a portion of the at least one training sample, the full k-space data may include first data of each of the plurality of k-space lines, and the predicted full k-space data may include second data of each of the plurality of k-space lines. The generating a comparison result between the predicted full k-space data and the full k-space data of the training sample may include determining one or more second k-space lines by removing the plurality of first k-space lines from the plurality of k-space lines. The generating a comparison result between the predicted full k-space data and the full k-space data of the training sample may further include, for each of the one or more second k-space lines, determining a difference between the first data of the second k-space line and the second data of the second k-space line, the comparison result comprising the difference corresponding to the each of the one or more second k-space lines.

In some embodiments, in response to determining that the intermediate subsampling model does not satisfy the termination condition, the at least one iteration of the one or more iteration may include updating, based on the at least a portion of the at least one training sample, the intermediate MRI reconstruction model.

In some embodiments, the intermediate MRI reconstruction model may be an updated intermediate subsampling model generated in a previous iteration. In response to determining that the intermediate subsampling model satisfies the termination condition, the at least one iteration of the one or more iterations may include designating the intermediate subsampling model as the subsampling model, and designating the intermediate MRI reconstruction model as the MRI reconstruction model.

In some embodiments, the intermediate MRI reconstruction model may be the preliminary MRI reconstruction model. In response to determining that the intermediate subsampling model satisfies the termination condition, the at least one iteration of the one or more iterations may further include designating the intermediate subsampling model as the subsampling model, and generating the MRI reconstruction model by updating the intermediate MRI reconstruction model based on the at least a portion of the at least one training sample.

In some embodiments, the full MRI data of each of the at least one training sample may be acquired based on a first MRI sequence. The subsampling model may correspond to the first MRI sequence. The at least one processor may be further configured to direct the system to perform the operations. The operations may include obtaining at least one second training sample each of which includes second full MRI data acquired based on a second MRI sequence. The operations may include, for each of the at least one second training sample, generating a reference image corresponding to the first MRI sequence based on the subsampling model and the MRI reconstruction model. The operations may also include obtaining a second preliminary subsampling model and a second preliminary MRI reconstruction model. The operations may further include generating a second subsampling model and a second MRI reconstruction model corresponding to the second MRI sequence by jointly training the second preliminary subsampling model and the second preliminary MRI reconstruction model using the at least one second training sample and the at least one reference image. The second subsampling model may be the trained second preliminary subsampling model, and the second MRI reconstruction model may be the trained second preliminary MRI reconstruction model.

In some embodiments, for each of the at least one second training sample, the generating a reference image based on the subsampling model and the MRI reconstruction model may include generating a subsampled MRI image based on the subsampling model and the second full MRI data of the second training sample, and generating the reference image by processing the subsampled MRI image using the MRI reconstruction model.

In some embodiments, the at least one processor may be further configured to direct the system to perform the operations. The operations may include obtaining target subsampled k-space data of a subject by performing an MRI scan on the subject according to the subsampling model. The operations may include generating a target subsampled MRI image of the subject based on the target subsampled k-space data. The operations may further include generating a target full MRI image of the subject by processing the target subsampled MRI image using the MRI reconstruction model.

In some embodiments, the MRI reconstruction model may include at least one of a convolution network or a generative adversarial network (GAN).

Another aspect of the present disclosure relates to a system for Magnetic Resonance Imaging (MRI). The system may include at least one storage device including a set of instructions and at least one processor in communication with the at least one storage device. When executing the set of instructions, the at least one processor may be directed to perform operations. The operations may include obtaining target subsampled k-space data of a subject by performing an MRI scan on the subject according to a subsampling model corresponding to an MRI reconstruction model. The operations may include generating a target subsampled MRI image of the subject based on the target subsampled k-space data. The operations may further include generating a target full MRI image of the subject by processing the target subsampled MRI image using the MRI reconstruction model, wherein the subsampling model and the MRI reconstruction model are jointly trained using at least one training sample.

In some embodiments, the subsampling model and the MRI reconstruction model may be jointly trained according to a model training process. The model training process may include obtaining the at least one training sample each of which includes full MRI data. The model training process may include obtaining a preliminary subsampling model and a preliminary MRI reconstruction model. The model training process may further include generating the subsampling model corresponding to the MRI reconstruction model by jointly training the preliminary subsampling model and the preliminary MRI reconstruction model using the at least one training sample. The subsampling model may be the trained preliminary subsampling model, and the MRI reconstruction model may be at least a portion of the trained preliminary MRI reconstruction model.

A further aspect of the present disclosure relates to a method for Magnetic Resonance Imaging (MRI). The method may be implemented on a computing device including at least one processor and at least one storage device. The method may include obtaining at least one training sample each of which includes full MRI data. The method may include obtaining a preliminary subsampling model and a preliminary MRI reconstruction model. The method may further include generating a subsampling model corresponding to an MRI reconstruction model by jointly training the preliminary subsampling model and the preliminary MRI reconstruction model using the at least one training sample. The subsampling model being the trained preliminary subsampling model, and the MRI reconstruction model being at least a portion of the trained preliminary MRI reconstruction model.

A further aspect of the present disclosure relates to a method for Magnetic Resonance Imaging (MRI). The method may be implemented on a computing device including at least one processor and at least one storage device. The method may include obtaining target subsampled k-space data of a subject by performing an MRI scan on the subject according to a subsampling model corresponding to an MRI reconstruction model. The method may include generating a target subsampled MRI image of the subject based on the target subsampled k-space data. The method may further include generating a target full MRI image of the subject by processing the target subsampled MRI image using the MRI reconstruction model, wherein the subsampling model and the MRI reconstruction model are jointly trained using at least one training sample.

A still further aspect of the present disclosure relates to a non-transitory computer readable medium including executable instructions. When the executable instructions are executed by at least one processor, the executable instructions may direct the at least one processor to perform a method. The method may include obtaining at least one training sample each of which includes full MRI data. The method may include obtaining a preliminary subsampling model and a preliminary MRI reconstruction model. The method may further include generating a subsampling model corresponding to an MRI reconstruction model by jointly training the preliminary subsampling model and the preliminary MRI reconstruction model using the at least one training sample. The subsampling model may be the trained preliminary subsampling model, and the MRI reconstruction model may be at least a portion of the trained preliminary MRI reconstruction model.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 14 is a schematic diagram illustrating an exemplary process for generating a target full MRI image of a target subject according to some embodiments of the present disclosure.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "device," "unit," "module," and/or "block" used herein are one method to distinguish different components, elements, parts, sections, or assembly of different levels in ascending order. However, the terms may be displaced by another expression if they achieve the same purpose.

Figure 2:
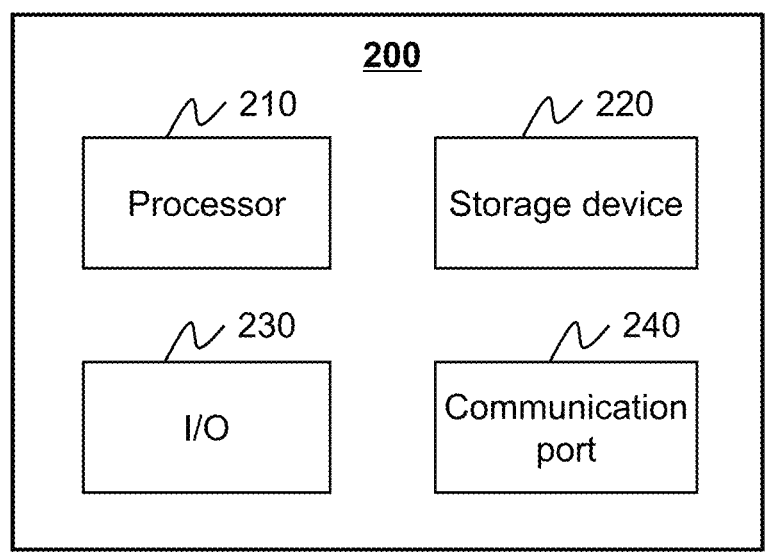
FIG. 2 is a schematic diagram illustrating exemplary hardware and/or software components of a computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may apply to a system, a device, or a portion thereof.

It will be understood that when a unit, device, module or block is referred to as being "on," "connected to," or "coupled to," another unit, device, module, or block, it may be directly on, connected or coupled to, or communicate with the other unit, device, module, or block, or an intervening unit, device, module, or block may be present, unless the context clearly indicates otherwise. As used herein, the term "and/or" includes any and all combinations of one or more of the associated listed items. The term "pixel" and "voxel" in the present disclosure are used interchangeably to refer to an element in an image. The term "image" in the present disclosure is used to refer to images of various forms, including a 2-dimensional image, a 3-dimensional image, a 4-dimensional image, etc.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments of the present disclosure. It is to be expressly understood the operations of the flowcharts may be implemented not in order. Conversely, the operations may be implemented in an inverted order, or simultaneously. Moreover, one or more other operations may be added to the flowcharts. One or more operations may be removed from the flowcharts.

Moreover, while the systems and methods disclosed in the present disclosure are described primarily regarding image reconstruction in an MRI system. It should be understood that this is only for illustration purposes. The systems and methods of the present disclosure may be applied to reconstruct image data acquired in different scenarios and/or for different purposes (e.g., safety monitoring, filming, or photography) and/or by different image devices (e.g., a computed tomography (CT) scanner, a positron emission tomography (PET) scanner).

For example, the systems and methods of the present disclosure may be applied to any other kind of medical imaging system. In some embodiments, the imaging system may include a single modality imaging system and/or a multi-modality imaging system. The single modality imaging system may include, for example, the MRI system. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc.

MRI systems are widely used in medical diagnosis and/or treatment by exploiting a powerful magnetic field and radio frequency (RF) techniques. Normally, full k-space data of a subject may need to be collected for reconstructing a full MRI image of the subject. In order to accelerate the data acquisition and reduce the scan time, a fraction of the full k-space data (i.e., a set of subsampled k-space data) may be acquired by subsampling with, for example, a reduced number of k-space sampling steps, a reduced number of samples per line, a reduced number of lines per blade, a reduced number of blades per acquisition, or the like, or any combination thereof.

In some embodiments, the subsampling approach may be performed according to a subsampling model (or referred to as a subsampling pattern). The subsampling model may define how to perform subsampling during an MRI scan of the subject. For example, the full k-space data may be represented as data corresponding to a plurality of k-space lines (e.g., phase-encoding lines, radial lines). The subsampling model may define a plurality of target k-space lines that need to be sampled among the plurality of k-space lines, the sampling order of the target k-space lines, or the like, or any combination thereof. In some embodiments, during the MRI scan of the subject, the sampling frequency may be lower than twice the highest frequency of MR signals to be sampled.

In some embodiments, after the set of subsampled k-space data of the subject is acquired during the MRI scan according to the subsampling model, a subsampled MRI image may be generated based on the set of subsampled k-space data by, for example, performing an inverse Fourier transformation on the set of subsampled k-space data. Further, the subsampled MRI image may need to be reconstructed into a predicted full MRI image of the subject. Recently, a machine learning technique, such as a machine learning model, has been utilized for reconstructing the subsampled MRI image into the predicted full MRI image. However, the subsampling model used by conventional subsampling approaches may normally be an arbitrary subsampling model, or a default setting of an MRI system, or set manually by a user (e.g., a doctor, a radiologist) of the MRI system. An image reconstructed based on data acquired by the subsampling model may have a lot of artifacts. In addition, a same subsampling model may be utilized for different types of machine learning models, which may lead to a low reconstruction accuracy.

In order to improve the reconstruction accuracy in MRI, an aspect of the present disclosure provides systems and methods for generating a subsampling model corresponding to an MRI reconstruction model. The systems may obtain at least one training sample each of which includes full MRI data. The systems may also obtain a preliminary subsampling model and a preliminary MRI reconstruction model. Further, the systems may generate the subsampling model corresponding to the MRI reconstruction model by jointly training the preliminary subsampling model and the preliminary MRI reconstruction model using the at least one training sample. The subsampling model may be the trained preliminary subsampling model, and the MRI reconstruction model may be at least a portion of the trained preliminary MRI reconstruction model.

By jointly training the preliminary subsampling model and the preliminary MRI reconstruction model, the generated subsampling model may be regarded as a specific subsampling model that matches and be suitable for the generated MRI reconstruction model. The reliability and the accuracy of the subsampling model and the MRI reconstruction model may be improved. In this way, the sampling efficiency and/or accuracy in an MRI scan performed based on the subsampling model may be improved, and a full MRI image reconstructed based on the MRI reconstruction model may have an improved accuracy.

According to some embodiments of the present disclosure, an MRI scan of a subject may be implemented according to a plurality of MRI sequences. Because that different types of MRI sequences may have different characteristics (e.g., different pulse sequence parameters) and images generated by different types of MRI sequences may have different characteristics, a specific subsampling model and a specific MRI reconstruction model may be generated for each MRI sequence. This may further improve the accuracy of the generated subsampling models and the MRI reconstruction models of the MRI sequences. Moreover, in some embodiments, during the training process of the subsampling model and the MRI reconstruction model corresponding to a certain MRI sequence, one or more reference images may be generated based on the trained subsampling model(s) and the trained MRI reconstruction model(s) corresponding to other MRI sequence(s). The utilization of the reference image(s) may facilitate image reconstruction in the training process of the subsampling model and the MRI reconstruction model corresponding to the certain MRI sequence, and improve the training efficiency (e.g., by accelerating model convergence) and/or the training accuracy.

Figure 1:
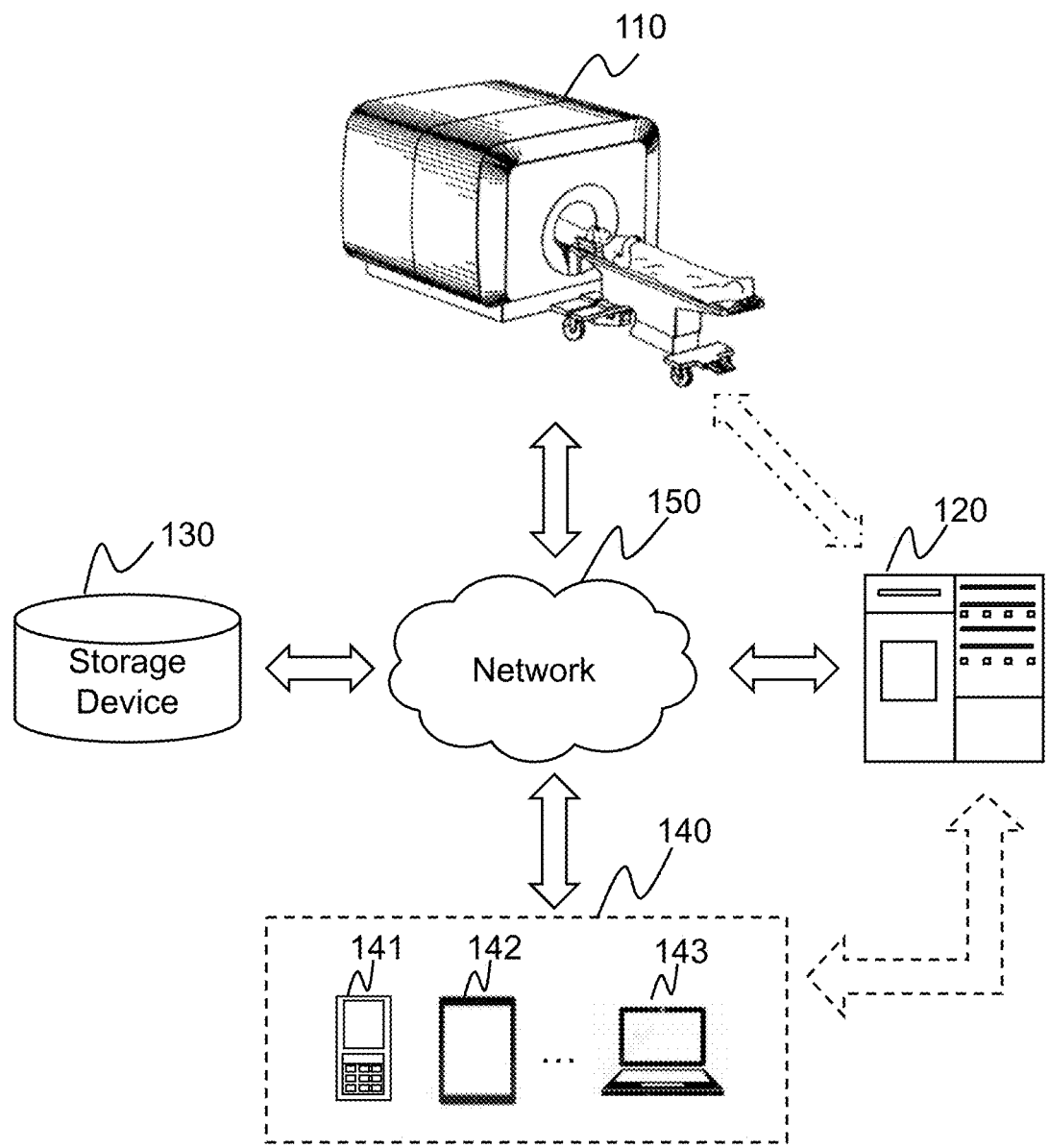
FIG. 1 is a schematic diagram illustrating an exemplary MRI system according to some embodiments of the present disclosure.

FIG. 1 is a schematic diagram illustrating an exemplary MRI system 100 according to some embodiments of the present disclosure. It should be noted that the MRI system 100 is merely provided as an exemplary imaging system, and not intended to limit the scope of the present disclosure. The exemplary methods described in the present disclosure may be applied in other imaging systems, such as a CT system, a PET system, a PET-MRI system, or the like.

As shown in FIG. 1, the MRI system 100 may include an MR scanner 110, a processing device 120, a storage device 130, one or more terminals 140, and a network 150. In some embodiments, the MR scanner 110, the processing device 120, the storage device 130, and/or the terminal(s) 140 may be connected to and/or communicate with each other via a wireless connection, a wired connection, or a combination thereof. The connections between the components in the MRI system 100 may be variable. For example, the MR scanner 110 may be connected to the processing device 120 through the network 150. As another example, the MR scanner 110 may be connected to the processing device 120 directly.

The MR scanner 110 may be configured to scan a subject (or a part of the subject) to acquire image data, such as MR signals associated with the subject. For example, the MR scanner 110 may detect a plurality of MR signals by applying an MRI sequence on the subject. In some embodiments, the MR scanner 110 may include, for example, a magnetic body, a gradient coil, an RF coil, etc. In some embodiments, the MR scanner 110 may be a permanent magnet MR scanner, a superconducting electromagnet MR scanner, or a resistive electromagnet MR scanner, etc., according to types of the magnetic body. In some embodiments, the MR scanner 110 may be a high-field MR scanner, a mid-field MR scanner, and a low-field MR scanner, etc., according to the intensity of the magnetic field.

In the present disclosure, "subject" and "object" are used interchangeably. The subject may be biological or non-biological. For example, the subject may include a patient, a man-made subject, etc. As another example, the subject may include a specific portion, organ, tissue, and/or a physical point of the patient. For example, the subject may include head, brain, neck, body, shoulder, arm, thorax, cardiac, stomach, blood vessel, soft tissue, knee, feet, or the like, or a combination thereof.

In some embodiments, the processing device 120 may be a single server or a server group. The server group may be centralized or distributed. The processing device 120 may process data and/or information obtained from the MR scanner 110, the storage device 130, and/or the terminal(s) 140. For example, the processing device 120 may obtain at least one training sample, and generate a subsampling model corresponding to an MRI reconstruction model by jointly training a preliminary subsampling model and a preliminary MRI reconstruction model using the at least one training sample. As another example, the processing device 120 may apply the subsampling model and the MRI reconstruction model to generate a target full MRI image of a target subject.

In some embodiments, a trained model (e.g., the subsampling model and/or the MRI reconstruction model) may be generated by a processing device, while the application of the trained model may be performed on a different processing device. In some embodiments, the trained model may be generated by a processing device of a system different from the MRI system 100 or a server different from the processing device 120 on which the application of the trained model is performed. For instance, the subsampling model and/or the MRI reconstruction model may be generated by a first system of a vendor who provides and/or maintains such a trained model, while the generation of the target full MRI image based on the provided trained model may be performed on a second system of a client of the vendor. In some embodiments, the application of the trained model may be performed online in response to a request for generating a target full MRI image of a target subject. In some embodiments, the trained model may be determined or generated offline.

In some embodiments, the trained model may be determined and/or updated (or maintained) by, e.g., the manufacturer of the MR scanner 110 or a vendor. For instance, the manufacturer or the vendor may load the subsampling model and/or the MRI reconstruction model into the MRI system 100 or a portion thereof (e.g., the processing device 120) before or during the installation of the MR scanner 110 and/or the processing device 120, and maintain or update the subsampling model and/or the MRI reconstruction model from time to time (periodically or not). The maintenance or update may be achieved by installing a program stored on a storage device (e.g., a compact disc, a USB drive, etc.) or retrieved from an external source (e.g., a server maintained by the manufacturer or vendor) via the network 150. The program may include a new model (e.g., a newly trained model) or a portion of a model that substitute or supplement a corresponding portion of the model.

In some embodiments, the processing device 120 may be local or remote from the MRI system 100. For example, the processing device 120 may access information and/or data from the MR scanner 110, the storage device 130, and/or the terminal(s) 140 via the network 150. As another example, the processing device 120 may be directly connected to the MR scanner 110, the terminal(s) 140, and/or the storage device 130 to access information and/or data. In some embodiments, the processing device 120 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 120 may be implemented by a computing device 200 having one or more components as described in connection with FIG. 2.

The storage device 130 may store data, instructions, and/or any other information. In some embodiments, the storage device 130 may store data obtained from the MR scanner 110, the processing device 120, and/or the terminal(s) 140. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or a combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc. In some embodiments, the storage device 130 may be implemented on a cloud platform as described elsewhere in the disclosure.

In some embodiments, the storage device 130 may be connected to the network 150 to communicate with one or more other components in the MRI system 100 (e.g., the MR scanner 110, the processing device 120, and/or the terminal(s) 140). One or more components of the MRI system 100 may access the data or instructions stored in the storage device 130 via the network 150. In some embodiments, the storage device 130 may be part of the processing device 120 or the terminal(s) 140.

The terminal(s) 140 may be configured to enable a user interaction between a user and the MRI system 100. For example, the terminal(s) 140 may receive an instruction to cause the MR scanner 110 to scan the subject from the user. As another example, the terminal(s) 140 may receive a processing result (e.g., a reconstructed MRI image of a target subject) from the processing device 120 and display the processing result to the user. In some embodiments, the terminal(s) 140 may be connected to and/or communicate with the MR scanner 110, the processing device 120, and/or the storage device 130. In some embodiments, the terminal(s) 140 may include a mobile device 141, a tablet computer 142, a laptop computer 143, or the like, or a combination thereof. For example, the mobile device 141 may include a mobile phone, a personal digital assistant (PDA), a gaming device, a navigation device, a point of sale (POS) device, a laptop, a tablet computer, a desktop, or the like, or a combination thereof. In some embodiments, the terminal(s) 140 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 120 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 140 may be part of the processing device 120 or the MR scanner 110.

The network 150 may include any suitable network that can facilitate the exchange of information and/or data for the MRI system 100. In some embodiments, one or more components of the MRI system 100 (e.g., the MR scanner 110, the processing device 120, the storage device 130, the terminal(s) 140, etc.) may communicate information and/or data with one or more other components of the MRI system 100 via the network 150. For example, the processing device 120 may obtain image data (e.g., MR signals) from the MR scanner 110 via the network 150. As another example, the processing device 120 may obtain user instructions from the terminal(s) 140 via the network 150.

The network 150 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, or the like, or a combination thereof. For example, the network 150 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or a combination thereof. In some embodiments, the network 150 may include one or more network access points. For example, the network 150 may include wired and/or wireless network access points such as base stations and/or internet exchange points through which one or more components of the MRI system 100 may be connected to the network 150 to exchange data and/or information.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. In some embodiments, the MRI system 100 may include one or more additional components and/or one or more components described above may be omitted. Additionally or alternatively, two or more components of the MRI system 100 may be integrated into a single component. For example, the processing device 120 may be integrated into the MR scanner 110. As another example, a component of the MRI system 100 may be replaced by another component that can implement the functions of the component. In some embodiments, the storage device 130 may be a data storage including cloud-computing platforms, such as a public cloud, a private cloud, a community, and hybrid cloud, etc. However, those variations and modifications do not depart the scope of the present disclosure.

FIG. 2 is a schematic diagram illustrating exemplary hardware and/or software components of a computing device 200 according to some embodiments of the present disclosure. The computing device 200 may be used to implement any component of the MRI system 100 as described herein. For example, the processing device 120 and/or a terminal 140 may be implemented on the computing device 200, respectively, via its hardware, software program, firmware, or a combination thereof. Although only one such computing device is shown, for convenience, the computer functions relating to the MRI system 100 as described herein may be implemented in a distributed fashion on a number of similar platforms, to distribute the processing load. As illustrated in FIG. 2, the computing device 200 may include a processor 210, a storage device 220, an input/output (I/O) 230, and a communication port 240.

The processor 210 may execute computer instructions (e.g., program code) and perform functions of the processing device 120 in accordance with techniques described herein. The computer instructions may include, for example, routines, programs, objects, components, data structures, procedures, modules, and functions, which perform particular functions described herein. For example, the processor 210 may process image data of a subject obtained from the MR scanner 110, the storage device 130, terminal(s) 140, and/or any other component of the MRI system 100. As another example, the processor 210 may generate an MRI image of the subject based on the (processed) image data of the subject.

In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 200. However, it should be noted that the computing device 200 in the present disclosure may also include multiple processors. The operations and/or method steps that are performed by one processor as described in the present disclosure may also be jointly or separately performed by the multiple processors. For example, if in the present disclosure the processor of the computing device 200 executes both operation A and operation B, it should be understood that operation A and operation B may also be performed by two or more different processors jointly or separately in the computing device 200 (e.g., a first processor executes operation A and a second processor executes operation B, or the first and second processors jointly execute operations A and B).

The storage device 220 may store data/information obtained from the MR scanner 110, the storage device 130, the terminal(s) 140, and/or any other component of the MRI system 100. In some embodiments, the storage device 220 may include a mass storage device, a removable storage device, a volatile read-and-write memory, a read-only memory (ROM), or the like, or a combination thereof. In some embodiments, the storage device 220 may store one or more programs and/or instructions to perform exemplary methods described in the present disclosure. For example, the storage device 220 may store a program for the processing device 120 to execute to generate a trained model (e.g., a subsampling model and/or an MRI reconstruction model). As another example, the storage device 220 may store a program for the processing device 120 to execute to apply the trained model (e.g., the subsampling model and/or the MRI reconstruction model) to generate a target full MRI image of a target subject.

The I/O 230 may input and/or output signals, data, information, etc. In some embodiments, the I/O 230 may enable a user interaction with the processing device 120. In some embodiments, the I/O 230 may include an input device and an output device. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to another component (e.g., the processing device 120) via, for example, a bus, for further processing. Other types of the input device may include a cursor control device, such as a mouse, a trackball, or cursor direction keys, etc. The output device may include a display (e.g., a liquid crystal display (LCD), a light-emitting diode (LED)-based display, a flat panel display, a curved screen, a television device, a cathode ray tube (CRT), a touch screen), a speaker, a printer, or the like, or a combination thereof.

The communication port 240 may be connected to a network (e.g., the network 150) to facilitate data communications. The communication port 240 may establish connections between the processing device 120 and one or more components of the MRI system 100 (e.g., the MR scanner 110, the storage device 130, and/or the terminal(s) 140). The connection may be a wired connection, a wireless connection, any other communication connection that can enable data transmission and/or reception, and/or a combination of these connections. The wired connection may include, for example, an electrical cable, an optical cable, a telephone wire, or the like, or a combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
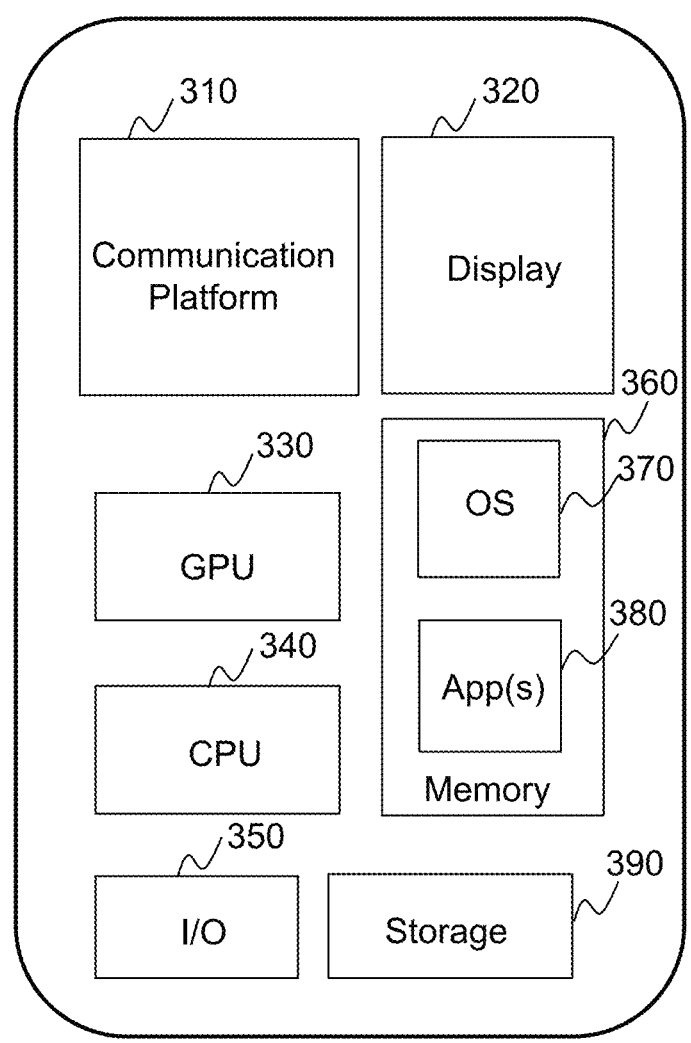
FIG. 3 is a schematic diagram illustrating exemplary hardware and/or software components of a mobile device according to some embodiments of the present disclosure.

FIG. 3 is a schematic diagram illustrating exemplary hardware and/or software components of a mobile device 300 according to some embodiments of the present disclosure. In some embodiments, one or more components of the MRI system 100 may be implemented on one or more components of the mobile device 300. Merely by way of example, a terminal 140 may be implemented on one or more components of the mobile device 300.

As illustrated in FIG. 3, the mobile device 300 may include a communication platform 310, a display 320, a graphics processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information relating to the MRI system 100. User interactions with the information stream may be achieved via the I/O 350 and provided to the processing device 120 and/or other components of the MRI system 100 via the network 150.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
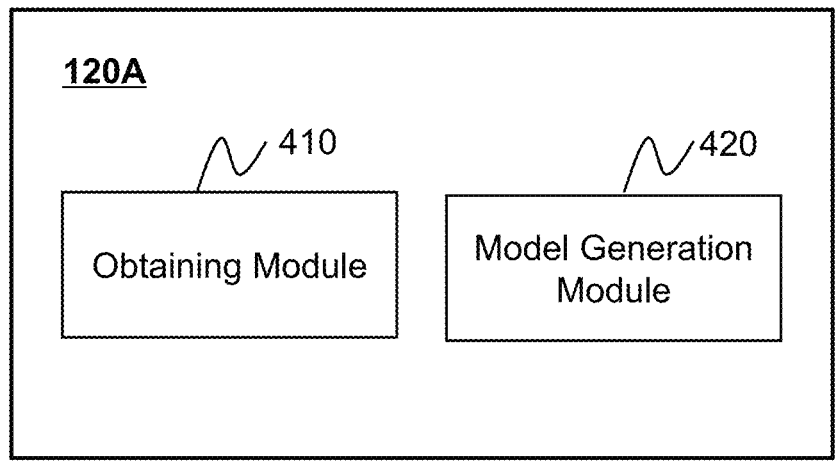
FIGS. 4A and 4B are block diagrams illustrating exemplary processing devices according to some embodiments of the present disclosure.
Figure 4B:
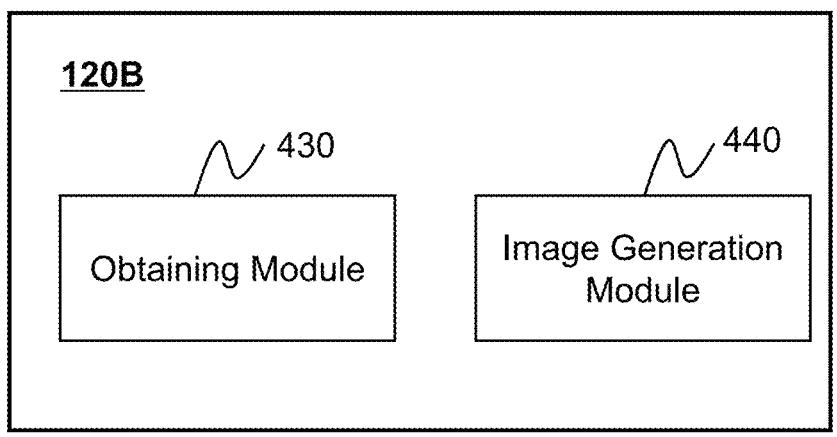

FIGS. 4A and 4B are block diagrams illustrating exemplary processing devices according to some embodiments of the present disclosure. The processing devices 120A and 120B may be exemplary embodiments of the processing device 120 as described in connection with FIG. 1. In some embodiments, the processing device 120A may be configured to generate a subsampling model corresponding to an MRI reconstruction model. The processing device 120B may be configured to apply the subsampling model and the MRI reconstruction model in generating a target full MRI image of a target subject. In some embodiments, the processing devices 120A and 120B may be respectively implemented on a processing unit (e.g., a processor 210 illustrated in FIG. 2 or a CPU 340 as illustrated in FIG. 3). Merely by way of example, the processing devices 120A may be implemented on the computing device 200, and the processing device 120B may be implemented on a CPU 340 of a terminal device. Alternatively, the processing devices 120A and 120B may be implemented on a same computing device 200 or a same CPU 340. For example, the processing devices 120A and 1206 may be implemented on a same computing device 200.

As shown in FIG. 4A, the processing device 120A may include an obtaining module 410 and a model generation module 420.

The obtaining module 410 may be configured to obtain information for generating the subsampling model and the MRI reconstruction model. For example, the obtaining module 410 may obtain at least one training sample each of which includes full MRI data. In some embodiments, a training sample may include full MRI data of a training subject. The full MRI data of the training subject may include a full MRI image, full k-space data, or the like, or any combination thereof. More descriptions regarding the obtaining of the at least one training sample may be found elsewhere in the present disclosure. See, e.g., operation 510 in FIG. 5 and relevant descriptions thereof. As another example, the obtaining module 410 may be configured to obtain a preliminary subsampling model and a preliminary MRI reconstruction model. The preliminary subsampling model may define a preliminary subsampling pattern before model updating or training. The preliminary MRI reconstruction model refers to a preliminary algorithm or a preliminary model (e.g., a preliminary machine learning model) for MRI reconstruction before model training or updating. More descriptions regarding the obtaining of the preliminary subsampling model and the preliminary MRI reconstruction model may be found elsewhere in the present disclosure. See, e.g., operation 520 in FIG. 5 and relevant descriptions thereof.

The model generation module 420 may be configured to generate the subsampling model corresponding to the MRI reconstruction model by jointly training the preliminary subsampling model and the preliminary MRI reconstruction model using the at least one training sample. More descriptions regarding the generation of the subsampling model corresponding to the MRI reconstruction model may be found elsewhere in the present disclosure. See, e.g., operation 530 in FIG. 5 and relevant descriptions thereof.

As shown in FIG. 4B, the processing device 120B may include an obtaining module 430 and an image generation module 440.

The obtaining module 430 may be configured to obtain target subsampled k-space data of a target subject by performing an MRI scan on the target subject according to a subsampling model. The subsampling model may define how to perform subsampling during an MRI scan of a subject. More descriptions regarding the obtaining of the target subsampled k-space data of the target subject may be found elsewhere in the present disclosure. See, e.g., operation 1410 in FIG. 14 and relevant descriptions thereof.

The image generation module 440 may be configured to generate a target subsampled MRI image of the target subject based on the target subsampled k-space data. More descriptions regarding the generation of the target subsampled MRI image of the target subject may be found elsewhere in the present disclosure. See, e.g., operation 1420 in FIG. 14 and relevant descriptions thereof. The image generation module 440 may be further configured to generate a target full MRI image of the target subject by processing the target subsampled MRI image using an MRI reconstruction model. More descriptions regarding the generation of the target full MRI image of the target subject may be found elsewhere in the present disclosure. See, e.g., operation 1430 in FIG. 14 and relevant descriptions thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120A and/or the processing device 120B may share two or more of the modules, and any one of the modules may be divided into two or more units. For instance, the processing devices 120A and 120B may share a same obtaining module; that is, the obtaining module 410 and the obtaining module 430 are a same module. In some embodiments, the processing device 120A and/or the processing device 120B may include one or more additional modules, such as a storage module (not shown) for storing data. In some embodiments, the processing device 120A and the processing device 120B may be integrated into one processing device 120.

Figure 5:
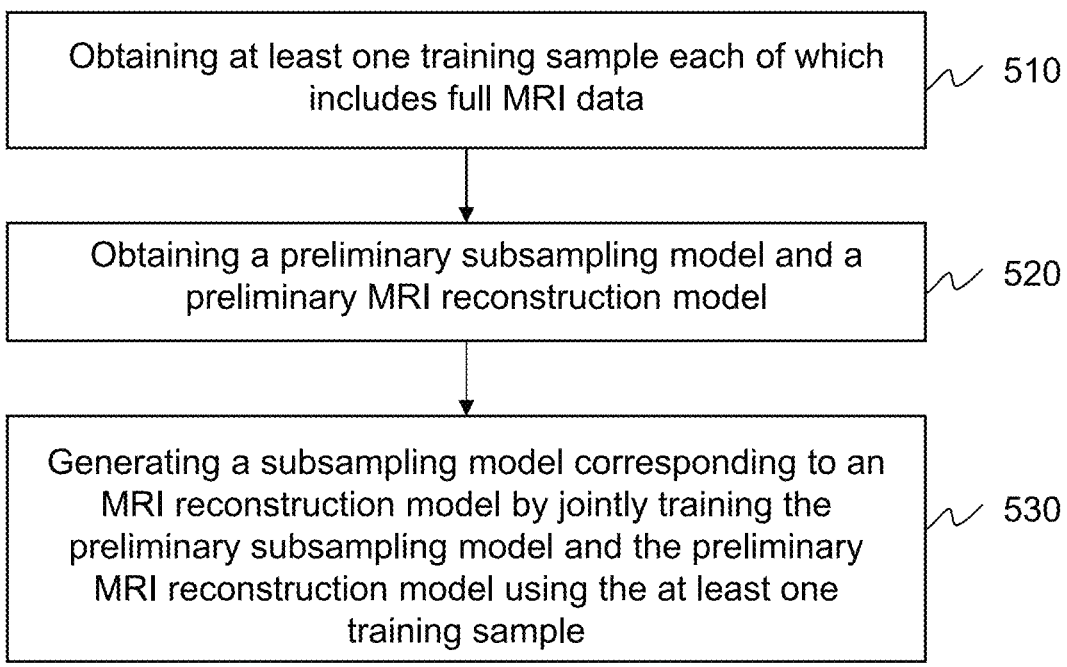
FIG. 5 is a flowchart illustrating an exemplary process for generating a subsampling model corresponding to an MRI reconstruction model according to some embodiment of the present disclosure.

FIG. 5 is a flowchart illustrating an exemplary process for generating a subsampling model corresponding to an MRI reconstruction model according to some embodiment of the present disclosure. In some embodiments, process 500 may be executed by the MRI system 100. For example, the process 500 may be implemented as a set of instructions (e.g., an application) stored in a storage device (e.g., the storage device 130, the storage device 220, and/or the storage 390). In some embodiments, the processing device 120A (e.g., the processor 210 of the computing device 200, the CPU 340 of the mobile device 300, and/or one or more modules illustrated in FIG. 4A) may execute the set of instructions and may accordingly be directed to perform the process 500. Alternatively, the process 500 may be performed by a computing device of a system of a vendor that provides and/or maintains such a trained model, wherein the system of the vendor is different from the MRI system 100. For illustration purposes, the following descriptions are described with reference to the implementation of the process 500 by the processing device 120A, and not intended to limit the scope of the present disclosure.

As described elsewhere in this disclosure, a subsampling approach may be utilized in an MRI scan to accelerate the data acquisition and reduce the scan time. For example, a set of subsampled k-space data of the subject may be acquired during the MRI scan according to a subsampling model (or referred to as a subsampling pattern), and a predicted full MRI image of the subject may be reconstructed based on the set of subsampled k-space data using a machine learning technique (e.g., a machine learning model). However, the subsampling model used by conventional approaches may normally be an arbitrary subsampling model, or a default setting of the MRI system 100, or set manually by a user (e.g., a doctor, a radiologist) of the MRI system 100. In addition, a same subsampling model may be utilized for different types of machine learning models, which may lead to a low reconstruction accuracy.

In order to improve the sampling efficiency and the reconstruction accuracy in MRI, an aspect of the present disclosure provides systems and methods for generating a subsampling model corresponding to an MRI reconstruction model. An MRI reconstruction model refers to a model (e.g., a machine learning model) or an algorithm for MRI reconstruction. For example, the MRI reconstruction model may be configured to reconstruct a subsampled MRI image (or subsampled k-space data) into a predicted full MRI image. In some embodiments, the subsampling model and the MRI reconstruction model may be jointly generated by performing the process 500 as described below, such that the subsampling model may be regarded as a specific subsampling model that matches and be suitable for the MRI reconstruction model.

In 510, the processing device 120A (e.g., the obtaining module 410) may obtain at least one training sample each of which includes full MRI data.

For example, a training sample may include full MRI data of a training subject. As used herein, a training subject may include a biological subject and/or a non-biological subject, such as a patient or a specific portion (e.g., an organ or a tissue) of the patient. The full MRI data of the training subject may include a full MRI image, full k-space data, or the like, or any combination thereof. The full k-space data may be acquired by performing an MRI scan on the subject based on an MRI sequence. The full MRI image may be reconstructed based on the full MRI data. In some embodiments, the MRI scan may be performed by an MRI scanner including a plurality of coil units. The full k-space data may include complex data acquired by the coil units or data generated by combining the complex data acquired by the coil units.

In some embodiments, the training subjects of different training samples may correspond to the same human part or different human parts. For example, the subsampling model may define a subsampling pattern for cardiac MR scans, and the MRI reconstruction model may be used to reconstruct a cardiac MRI image of a patient. The training subject of each training sample may be the heart of a patient.

In some embodiments, the full MRI data of different training samples may be acquired based on the same type of MRI sequence or different types of MRI sequences. For example, the full MRI data of different training samples may be acquired based on different types of MRI sequences including, such as, a spin-echo (SE) sequence, an inversion recovery (IR) sequence, a gradient echo (GRE) sequence, an echo-planar imaging (EPI), a fast spin-echo (FSE) sequence, a fluid-attenuated inversion recovery (FLAIR) sequence, or the like, or a combination thereof. In such cases, the generated subsampling model and/or the MRI reconstruction model may have a higher universality and be applicable for different types of MRI sequences.

As another example, the full MRI data of all training samples may be acquired based on a same MRI sequence, such as a fast spin-echo (FSE) sequence. In such cases, the generated subsampling model and/or the MRI reconstruction model may be specially designed for the fast spin-echo (FSE) sequence. Normally, different MRI sequences may have different pulse arrangements and be used to acquire different information with respect to a subject. For example, different MRI sequences may be used to acquire information relating to different quantitative parameters (e.g., T1, T2, etc.) of the subject. Generating a specialized subsampling model and/or an MRI reconstruction model for an MRI pulse sequence may improve the sampling efficiency and accuracy in an MRI scan performed based on the specialized subsampling model and the MRI sequence, and also the reconstruction accuracy of a full MRI image reconstructed based on the specialized MRI reconstruction mode.

In some embodiments, a training sample of a training subject may be previously generated and stored in a storage device (e.g., the storage device 130, the storage device 220, the storage 390, or an external database). The processing device 120A may retrieve the training sample directly from the storage device. In some embodiments, at least a portion of the training sample may be generated by the processing device 120A. For example, the processing device 120A may obtain MR signals of the training subject detected during an MR scan of the training subject from the MR scanner 110, and generate the full k-space data of the training subject by filling the MR signals into k-space. As another example, the processing device 120A may further reconstruct the full MRI image of the training subject based on the full k-space data of the training subject.

In 520, the processing device 120A (e.g., the obtaining module 410) may obtain a preliminary subsampling model and a preliminary MRI reconstruction model.

The preliminary subsampling model may define a preliminary subsampling pattern before model updating or training. In some embodiments, the preliminary subsampling model may be determined by the processing device 120A, for example, according to a random subsampling algorithm. Alternatively, the preliminary subsampling model may be determined according to a default setting of the MRI system 100 or set manually by a user (e.g., a doctor, a technician, etc.).

The preliminary MRI reconstruction model refers to a preliminary algorithm or a preliminary model (e.g., a preliminary machine learning model) for MRI reconstruction before model training or updating. In some embodiments, the preliminary MRI reconstruction model may be of a machine learning model, such as a neural network model. For example, the preliminary MRI reconstruction model may include a Convolutional Neural Network (CNN) model (e.g., a full CNN model, a Le network (LeNet) model, an Alex network (AlexNet) model, a Visual Geometry Group network (VGGNet) model), a recurrent neural network (RNN) model (e.g., a bi-directional RNN model, an Elman Neural Network model, a Jordan Neural Network model), a Generative Adversarial network (GAN) model, a U-net model, a Resnet model, a residual network model, a cascaded neural network model, or the like, or any combination thereof.

In some embodiments, the preliminary MRI reconstruction model may include one or more model parameters. For example, the preliminary MRI reconstruction model may be a CNN model and exemplary model parameters of the preliminary MRI reconstruction model may include the number (or count) of layers, the number (or count) of kernels, a kernel size, a stride, a padding of each convolutional layer, a loss function, or the like, or any combination thereof. Before training, the model parameter(s) may have their respective initial values. For example, the processing device 120A may initialize parameter value(s) of the model parameter(s) of the preliminary MRI reconstruction model.

In some embodiments, the preliminary MRI reconstruction model may be a GAN model that includes a generator and a discriminator. The generator may be configured to generate an image based on an input of the GAN model. The discriminator may be configured to generate a discrimination result between the image generated by the generator and a ground truth image (e.g., a full MRI image of a training sample). Alternatively, the preliminary MRI reconstruction model may be a full CNN model that may learn a mapping relationship between images. In some embodiments, the full CNN model may be capable of processing images with any image resolution or size.

In 530, the processing device 120A (e.g., the model generation module 420) may generate the subsampling model corresponding to the MRI reconstruction model by jointly training the preliminary subsampling model and the preliminary MRI reconstruction model using the at least one training sample. The trained preliminary subsampling model may be designated as the subsampling model, and at least a portion of the trained preliminary MRI reconstruction model may be designated as the MRI reconstruction model. For example, the preliminary MRI reconstruction model may be a GAN model that includes a generator and a discriminator. A trained generator of a trained GAN may be designated as the MRI reconstruction model. As yet another example, the preliminary MRI reconstruction model may be a full CNN model, and a trained full CNN model may be designated as the MRI reconstruction model.

In some embodiments, the processing device 120A may update the preliminary subsampling model and the preliminary MRI reconstruction model by performing one or more iterations. For illustration purposes, a current iteration of the iteration(s) is described in the following descriptions. The current iteration may be performed based on at least a portion of the at least one training sample. A same set or different sets of training samples may be used in different iterations in training the preliminary subsampling model and the preliminary MRI reconstruction model. In some embodiments, the current iteration may include one or more operations of process 600 as described in connection with FIG. 6 and/or one or more operations of process 700 as described in connection with FIG. 7.

It should be noted that the above description regarding the process 500 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, the MRI reconstruction model and/or the subsampling model may be stored in a storage device (e.g., the storage device 130) disclosed elsewhere in the present disclosure for further use. As another example, after the MRI reconstruction model and the subsampling model are generated, the processing device 120A may further test the MRI reconstruction model and/or the subsampling model using a set of testing samples. As a further example, the processing device 120A may update the MRI reconstruction model and/or the subsampling model periodically or irregularly based on one or more newly-generated training samples (e.g., new full MRI images and/or new full k-space data generated in medical diagnosis, etc.).

Figure 6:
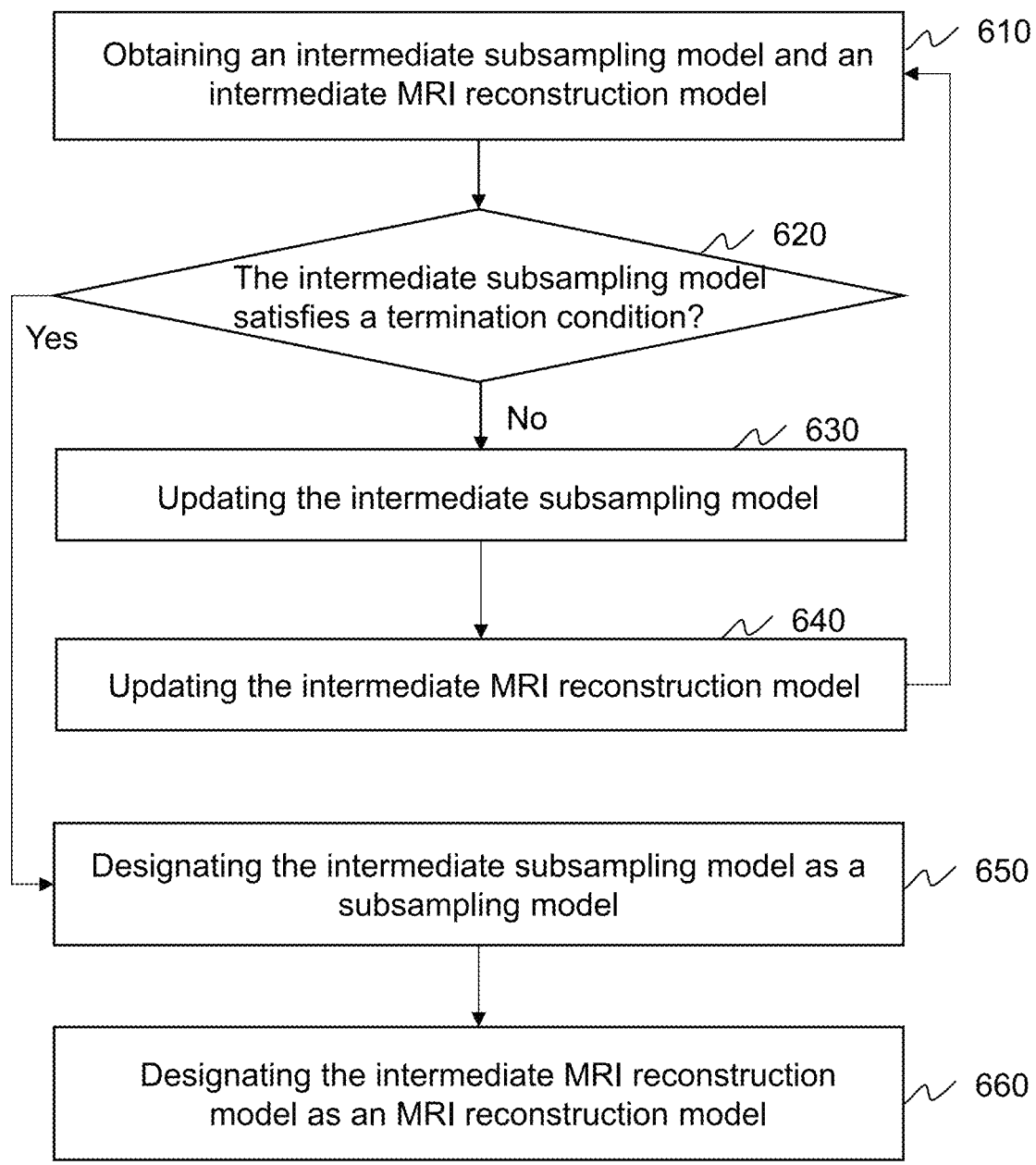
FIG. 6 is a flowchart illustrating an exemplary process for performing a current iteration of jointly training a preliminary subsampling model and a preliminary MRI reconstruction model according to some embodiments of the present disclosure.

FIG. 6 is a flowchart illustrating an exemplary process for performing a current iteration of jointly training a preliminary subsampling model and a preliminary MRI reconstruction model according to some embodiments of the present disclosure. In some embodiments, process 600 may be executed by the MRI system 100. For example, the process 600 may be implemented as a set of instructions (e.g., an application) stored in a storage device (e.g., the storage device 130, the storage device 220, and/or the storage 390). In some embodiments, the processing device 120A (e.g., the processor 210 of the computing device 200, the CPU 340 of the mobile device 300, and/or one or more modules illustrated in FIG. 4A) may execute the set of instructions and may accordingly be directed to perform the process 600. The operations of the illustrated process presented below are intended to be illustrative. In some embodiments, the process 600 may be accomplished with one or more additional operations not described and/or without one or more of the operations discussed. Additionally, the order of the operations of process 600 illustrated in FIG. 6 and described below is not intended to be limiting.

In some embodiments, the training process of the subsampling model and the MRI reconstruction model as described in connection with operation 530 in FIG. 5 may include one or more iterations. A current iteration of the training process may be performed according to the process 600 based on at least a portion of the at least one training sample. For the convenience of descriptions, the at least a portion of the at least one training sample used in the current iteration is referred to as target training sample(s).

In 610, the processing device 120A (e.g., the obtaining module 410) may obtain an intermediate subsampling model and an intermediate MRI reconstruction model based on the preliminary subsampling model and the preliminary MRI reconstruction model.

The intermediate subsampling model refers to an initial subsampling model to be processed (e.g., updated or analyzed) in the current iteration. The intermediate MRI reconstruction model refers to an initial MRI reconstruction model to be processed (e.g., updated or analyzed) in the current iteration.

In some embodiments, if the current iteration is the first iteration among the one or more iterations, the intermediate subsampling model and the intermediate MRI reconstruction model may be the preliminary subsampling model and the preliminary MRI reconstruction model as described in connection with operation 520, respectively. If the one or more iterations include a plurality of iterations and the current iteration is subsequent to the first iteration among the iterations, the intermediate subsampling model may be an updated intermediate subsampling model generated in a previous iteration, and the intermediate MRI reconstruction model may be an updated intermediate subsampling model generated in the previous iteration. For example, if the current iteration is the second iteration among the iterations, the intermediate subsampling model may be an updated intermediate subsampling model generated in the first iteration, and the intermediate MRI reconstruction model may be an updated intermediate subsampling model generated in the first iteration.

In 620, the processing device 120A (e.g., the model generation module 420) may determine whether the intermediate subsampling model satisfies a termination condition.

The termination condition may indicate whether the intermediate subsampling model is sufficiently updated. For example, the processing device 120A may evaluate the accuracy (or reliability) of the intermediate subsampling model based on the target training sample(s) and the intermediate MRI reconstruction model. If the accuracy (or reliability) of the intermediate subsampling model reaches a desired level, the processing device 120A may determine that the intermediate subsampling model satisfies the termination condition. In some embodiments, the accuracy (or reliability) of the intermediate subsampling model may be evaluated according to one or more operations of process 800 as described in connection with FIG. 8. For example, for each target training sample, the processing device 120A may generate a predicted full MRI image based on the full MRI data of the target training sample, the intermediate subsampling model, and the intermediate MRI reconstruction model. The processing device 120A may further determine whether the intermediate subsampling model satisfies the termination condition based on the predicted full MRI image of each target training sample. As another example, the processing device 120A may determine that the termination condition is satisfied if a specified number (or count) of iterations has been performed in the training process. It should be noted that the above descriptions of the termination condition are merely provided for illustration purposes, and not intended to be limiting.

In response to determining that the intermediate subsampling model satisfies the termination condition, the processing device 120A may proceed to operations 650 and 660. In 650, the processing device 120A (e.g., the model generation module 420) may designate the intermediate subsampling model as the subsampling model. In 660, the processing device 120A (e.g., the model generation module 420) may designate the intermediate MRI reconstruction model as the MRI reconstruction model.

In response to determining that the intermediate subsampling model does not satisfy the termination condition, the processing device 120A may proceed to operations 630 and 640. In 630, the processing device 120A (e.g., the model generation module 420) my update the intermediate subsampling model based on the intermediate MRI reconstruction model and the target training sample(s).

Merely by way of example, for each target training sample, the processing device 120A may generate predicted full k-space data based on the predicted full MRI image of the target training sample. For example, the processing device 120A may generate the predicted full k-space data of a target training sample by performing a Fourier transformation on the predicted full MRI image of the target training sample. The processing device 120A may also obtain full k-space data of the target training sample based on the full MRI data of the target training sample. The full k-space data of the target training sample may be included in the target training sample or be transformed from a full MRI image of the target training sample. Then, for each target training sample, the processing device 120A may generate a comparison result between the predicted full k-space data and the full k-space data of the target training sample. The processing device 120A may further update the intermediate subsampling model based on the comparison result of each target training sample.

The comparison result of a target training sample may indicate a difference between the predicted full k-space data and the full k-space data of the target training sample. For example, the difference may be determined by subtracting the predicted full k-space data from the full k-space data of the target training sample. As another example, the difference may be determined based on the predicted full k-space data and the full k-space data according to a least-square algorithm.

In some embodiments, the intermediate subsampling model may define a plurality of first k-space lines that need to be sampled among a plurality of k-space lines in full k-space. The full k-space data of the target training sample may include first data of each of the plurality of k-space lines, and the predicted full k-space data may include second data of each of the plurality of k-space lines. The processing device 120A may determine one or more second k-space lines by removing the plurality of first k-space lines from the plurality of k-space lines. In other words, the second k-space lines that are omitted from sampling according to the intermediate subsampling model may be determined. For each of the second k-space line(s), the processing device 120A may determine a difference between the first data and the second data of the second k-space line. The comparison result of the target training sample may include the difference corresponding to each of the one or more second k-space lines. For a certain second k-space line, the difference between the corresponding first and second data may be determined by subtracting the first data from the second data or subtracting the second data from the first data. Alternatively, the difference between the corresponding first and second data may be measured by, for example, an L1 norm difference, an L2 norm difference, a covariance value, or the like, or any combination thereof, of the first data and the second data.

In some embodiments, the processing device 120A may update the intermediate subsampling model according to the difference(s) corresponding to the one or more second k-space lines of each target training sample. For example, for each target training sample, the processing device 120A may select one or more second k-space lines with the largest X differences among the second k-space line(s), wherein X may be equal to any positive integer (e.g., 1, 2, 3, 5, etc.). The processing device 120A may update the intermediate subsampling model by adding the selected second k-space line(s) of each target training sample into the intermediate subsampling model. As another example, the processing device 120A may mark the one or more second k-space lines with the largest X differences for each training sample. The processing device 120A may determine the number of times that each second k-space line is marked, and select one or more second k-space lines having the top Y numbers of times (Y being any positive integer) among the second k-space line(s). The processing device 120A may further update the intermediate subsampling model by adding the selected second k-space line(s) into the intermediate subsampling model. In other words, the selected second k-space line(s) may be deemed as important k-space lines that need to be sampled, and the updated intermediate subsampling model may include both the first k-space line(s) and the selected second k-space line(s).

In 640, the processing device 120A (e.g., the model generation module 420) may update the intermediate MRI reconstruction model.

In some embodiments, the processing device 120A may determine a value of a loss function based on the intermediate subsampling model, the intermediate MRI reconstruction model, and the target training sample(s). The processing device 120 may further update value(s) of the model parameter(s) of the intermediate MRI reconstruction model based on the value of the loss function according to, for example, a backpropagation algorithm. The loss function may be used to evaluate the reliability and/or accuracy of the intermediate MRI reconstruction model in the current iteration, for example, the smaller the loss function is, the more reliable the intermediate MRI reconstruction model is. Exemplary loss functions may include an L1 loss function, a focal loss function, a log loss function, a cross-entropy loss function, a Dice loss function, etc. In some embodiments, the loss function may be determined by comparing the predicted full k-space data and the full k-space data of each target training sample. As another example, the loss function may be determined by comparing the predicted full MRI image and the full MRI image of each target training sample.

In some embodiments, the processing device 120A may update the intermediate MRI reconstruction model by performing a second iterative process including one or more second iterations until a second termination condition is satisfied in a certain second iteration. For example, the second termination condition may be that the value of the loss function is less than a threshold. The threshold may be default settings of the MRI system 100 or be adjustable under different situations. As another example, the second termination condition may be satisfied if the value of the cost function converges. The convergence may be deemed to have occurred if the variation of the values of the cost function in two or more consecutive iterations is smaller than a threshold (e.g., a constant). As still another example, the processing device 120A may determine that the second termination condition is satisfied if a specified number (or count) of second iterations has been performed.

In some embodiments, after 640, the processing device 120A may proceed to operation 610 to perform the next iteration until the termination condition is satisfied. The next iteration may be performed based on a same set or a different set of target training sample(s). After the termination condition is satisfied in a certain iteration, the intermediate subsampling model in the certain iteration may be designated as the subsampling model, and the intermediate MRI reconstruction model in the certain iteration may be designated as the MRI reconstruction model.

Figure 7:
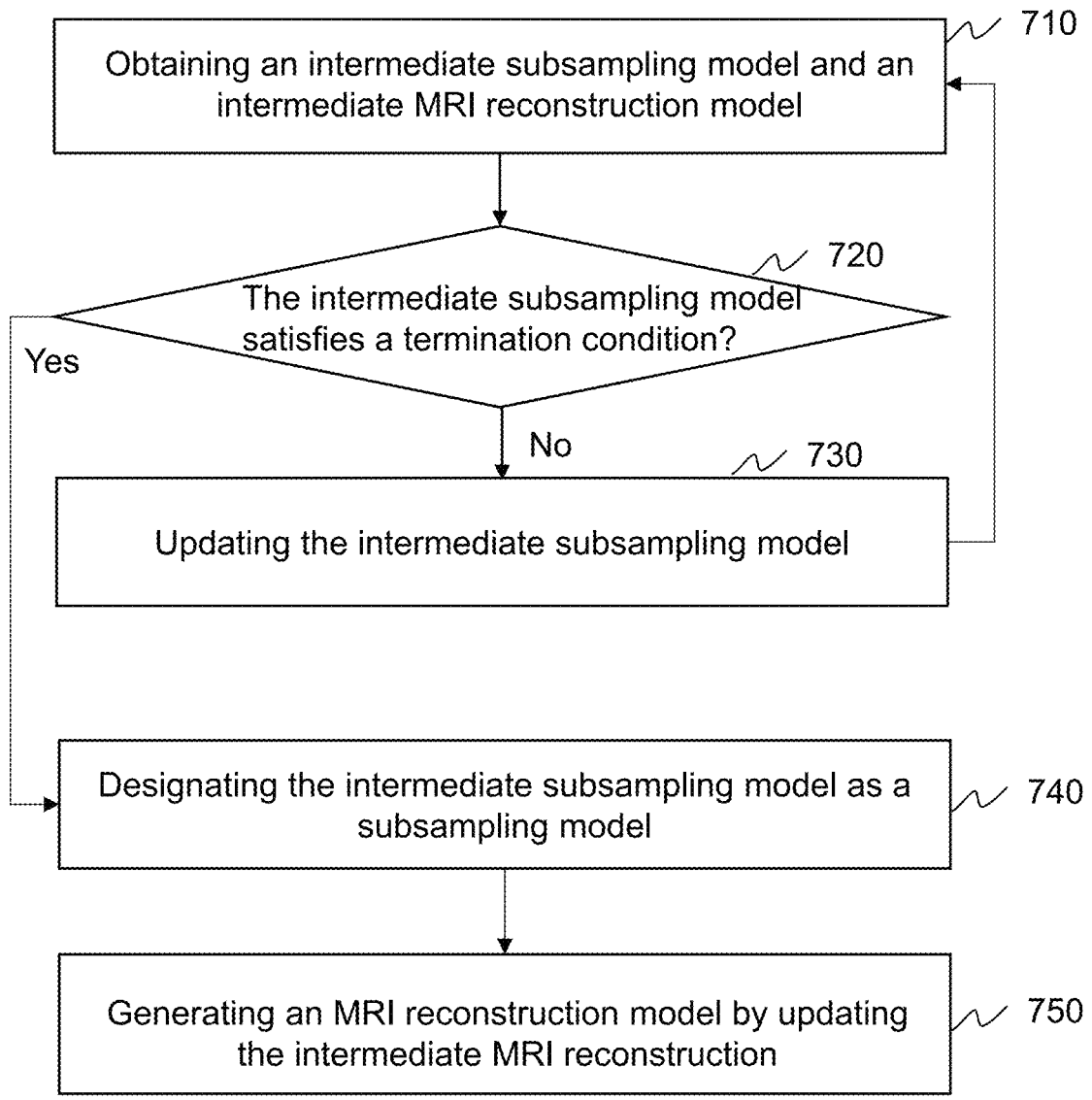
FIG. 7 is a flowchart illustrating an exemplary process for performing a current iteration of jointly training a preliminary subsampling model and a preliminary MRI reconstruction model according to some embodiments of the present disclosure.

In some embodiments, the current iteration of jointly training the preliminary subsampling model and the preliminary MRI reconstruction model may be performed by process 700 as shown in FIG. 7. The process 700 may be performed in a similar manner as the process 600, except for certain features. As described in connection with FIG. 6, in the first iteration of the training process, the intermediate MRI reconstruction model may be the preliminary MRI reconstruction model; in an iteration subsequent to the first iteration, the intermediate MRI reconstruction model may be an updated intermediate MRI reconstruction model generated in a previous iteration. If it is determined that the intermediate subsampling model does not satisfy the termination condition in the current iteration, the intermediate MRI reconstruction model may be updated. In other words, the value(s) of the model parameter(s) of the preliminary MRI reconstruction model determined in a previous iteration may be "inherited" to a next iteration, and the preliminary MRI reconstruction model may be updated for multiple times in the training process of FIG. 6.

Different from the process 600, the intermediate MRI reconstruction model obtained in each iteration (e.g., the first iteration, an iteration subsequent to the first iteration, etc.) may both be the preliminary MRI reconstruction model. If it is determined that the intermediate subsampling model does not satisfy the termination condition in the current iteration, the training process may proceed to a next iteration without updating the intermediate MRI reconstruction model. If it is determined that the intermediate subsampling model satisfies the termination condition in the current iteration, the intermediate MRI reconstruction model may be updated to generate the MRI reconstruction model.

The process 600 and the process 700 may have their respective advantages, and the processing device 120A or a user of the MRI system 100 may select one of them to jointly generate the subsampling model and the MRI reconstruction model according to an actual situation. For example, in the process 600, the preliminary MRI reconstruction model may be updated multiple times, thereby generating an MRI reconstruction model with a higher accuracy and reliability. In the process 700, the preliminary MRI reconstruction model may not need to be updated during each iteration, which may save the training time and improve the training efficiency.

In 710, the processing device 120A (e.g., the obtaining module 410) may obtain an intermediate subsampling model and an intermediate MRI reconstruction model.

Operation 710 may be performed in a similar manner as operation 610 as described in connection with FIG. 6, except that the intermediate MRI reconstruction model obtained in the first iteration or an iteration subsequent to the first iteration may both be the preliminary MRI reconstruction model.

In 720, the processing device 120A (e.g., the model generation module 420) may determine whether the intermediate subsampling model satisfies a termination condition. Operation 720 may be performed in a similar manner as operation 620 as described in connection with FIG. 6, and the descriptions thereof are not repeated here.

In response to determining that the intermediate subsampling model does not satisfy the termination condition, the processing device 120A may proceed to operation 730.

In 730, the processing device 120A (e.g., the model generation module 420) my update the intermediate subsampling model. Operation 730 may be performed in a similar manner as operation 630 as described in connection with FIG. 6, and the descriptions thereof are not repeated here.

In some embodiments, after 730, the processing device 120A may proceed to operation 710 to perform the next iteration until the termination condition is satisfied. The next iteration may be performed based on a same set or different set of target training sample(s). After the termination condition is satisfied in a certain iteration, the intermediate subsampling model in the certain iteration may be designated as the subsampling model.

In response to determining that the intermediate subsampling model satisfies the termination condition, the processing device 120A may proceed to operations 740 and 750.

In 740, the processing device 120A (e.g., the model generation module 420) may designate the intermediate subsampling model as the subsampling model. In 750, the processing device 120A (e.g., the model generation module 420) may generate the MRI reconstruction model by updating the intermediate MRI reconstruction model based on the target training sample(s). In some embodiments, the processing device 120A may update the intermediate MRI reconstruction model by performing a second iterative process as described in connection with 640.

It should be noted that the above descriptions regarding the processes 600 and 700 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, one or more other optional operations (e.g., a storing operation) may be added in the processes 600 and 700. In the storing operation, the processing device 120A may store information and/or data (e.g., a training sample, the subsampling model, the MRI reconstruction model, etc.) associated with the MRI system 100 in a storage device (e.g., the storage device 130) disclosed elsewhere in the present disclosure.

Figure 8:
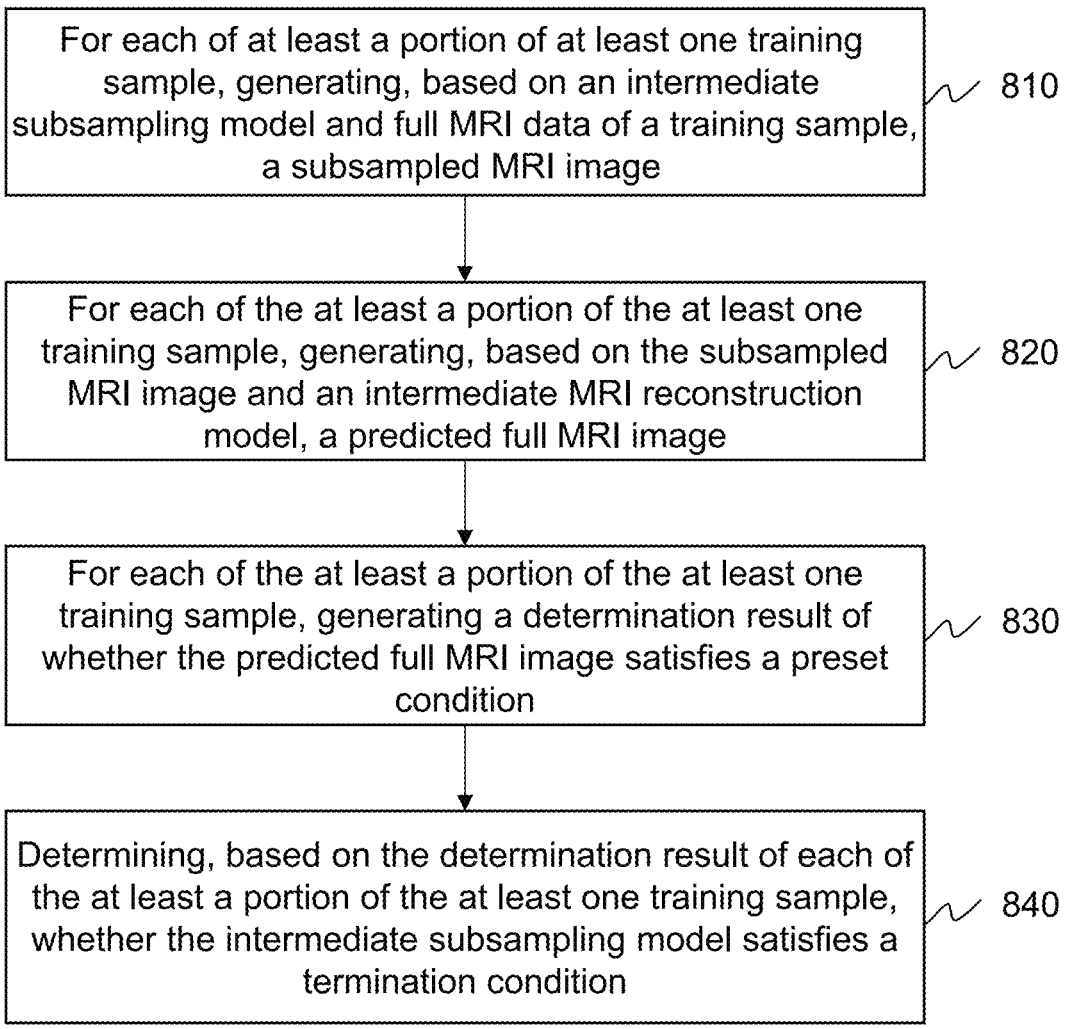
FIG. 8 is a flowchart illustrating an exemplary process for determining whether an intermediate subsampling model satisfies a termination condition in a current iteration according to some embodiments of the present disclosure.

FIG. 8 is a flowchart illustrating an exemplary process for determining whether an intermediate subsampling model satisfies a termination condition in a current iteration according to some embodiments of the present disclosure. In some embodiments, process 800 may be executed by the MRI system 100. For example, the process 800 may be implemented as a set of instructions (e.g., an application) stored in a storage device (e.g., the storage device 130, the storage device 220, and/or the storage 390). In some embodiments, the processing device 120A (e.g., the processor 210 of the computing device 200, the CPU 340 of the mobile device 300, and/or one or more modules illustrated in FIG. 4A) may execute the set of instructions and may accordingly be directed to perform the process 800. The operations of the illustrated process presented below are intended to be illustrative. In some embodiments, the process 800 may be accomplished with one or more additional operations not described and/or without one or more of the operations discussed. Additionally, the order of the operations of process 800 illustrated in FIG. 8 and described below is not intended to be limiting. In some embodiments, one or more operations of the process 800 may be performed to achieve at least part of operation 620 in FIG. 6 and/or operation 720 in FIG. 7.

In 810, for each of the at least a portion of the at least one training sample (i.e., each target training sample), the processing device 120A (e.g., the model generation module 420) may generate a subsampled MRI image based on the intermediate subsampling model obtained in the current iteration and full MRI data of the training sample.

As described elsewhere in this disclosure (e.g., FIG. 5 and the relevant descriptions), the full MRI data of a target training sample may a full MRI image, full k-space data, or the like, or any combination thereof. The processing device 120A may determine full k-space data of the target training sample based on the full MRI data of the target training sample. The processing device 120A may then determine a set of subsampled k-space data from the full k-space data of the target training sample according to the intermediate subsampling model. The processing device 120A may further generate the subsampled MRI image of the target training sample based on the set of subsampled k-space data.

Merely by way of example, the full k-space data of the target training sample may be represented as data corresponding to a plurality of k-space lines (e.g., phase-encoding lines, radial lines). The intermediate subsampling model may define a plurality of target k-space lines (or referred to as first k-space lines) that need to be sampled among the plurality of k-space lines. The processing device 120A may extract a portion of the full k-space data that corresponds to the target k-space lines, and designate the extracted portion of the full k-space data as the set of subsampled k-space data. As another example, the processing device 120A may generate the set of subsampled k-space data by performing a dot product on the intermediate subsampling model and the full k-space data of the target training sample. The processing device 120A may further generate the subsampled MRI image by performing an inverse Fourier transformation on the set of subsampled k-space data.

In 820, for each of the at least a portion of the at least one training sample (i.e., each target training sample), the processing device 120A (e.g., the model generation module 420) may generate, based on the subsampled MRI image and the intermediate MRI reconstruction model, a predicted full MRI image.

For example, for a target training sample, the corresponding subsampled MRI image may be inputted into the intermediate MRI reconstruction model, and the intermediate MRI reconstruction model may output the predicted full MRI image of the target training sample. As another example, the subsampled MRI image may be preprocessed (e.g., resampled, normalized, smoothed) before being inputted into the intermediate MRI reconstruction model. As yet another example, the intermediate MRI reconstruction model may generate an output in response to the input (e.g., the predicted full MRI image or the preprocessed predicted full MRI image), and the processing device 120A may post-process (e.g., resample, denormalize) the output to generate the predicted full MRI image. In some embodiments, the intermediate MRI reconstruction model may perform one or more processing operations (e.g., a convolution operation, a pooling operation, a feature extraction operation, or the like, or any combination thereof) on its input.

In 830, for each of the at least a portion of the at least one training sample (i.e., each target training sample), the processing device 120A (e.g., the model generation module 420) may generate a determination result of whether the predicted full MRI image satisfies a preset condition.

For example, for a target training sample, the processing device 120A may obtain a full MRI image based on the full MRI data of the target training sample, and determine a difference (or a degree of similarity) between the full MRI image and the predicted full MRI image of the target training sample.

As used herein, the difference between two images may be measured by one or more algorithms for image difference (or similarity) measurement. Exemplary algorithms for image difference (or similarity) measurement may include a Peak Signal to Noise Ratio (PSNR) algorithm, a Structural Similarity Index (SSIM) algorithm, a histogram algorithm, a perceptual hash algorithm, or the like, or any combination thereof. Merely by way of example, first value(s) of one or more parameters (e.g., the lightness, the contract ratio, the structure, the PSNR, the SSIM) of the predicted full MRI image may be determined. Second value(s) of the parameter(s) of the full MRI image may be determined. Difference(s) between the first value(s) and the second value(s) may be further determined to determine the difference between the two images. In some embodiments, a plurality of parameters may be utilized to determine the difference. For each of the parameters, the processing device 120A may determine a difference between the first value and the second value of the parameter. The processing device 120A may further determine the difference between the two images by determining a weighted sum of the differences corresponding to the parameters.

Further, for the target training sample, the processing device 120A may determine whether the predicted full MRI image of the target training sample satisfies the preset condition by determining whether the difference exceeds a threshold difference. The threshold difference may be determined according to a default setting of the MRI system 100, or automatically by the processing device 120A according to an actual need, or set manually by the user (e.g., a doctor, a technician, etc.). If the difference between the predicted full MRI image and the full MRI image does not exceed the threshold difference, the processing device 120A may generate a determination result that the predicted full MRI image of the target training sample satisfies the preset condition. If the difference between the predicted full MRI image and the full MRI image exceeds the threshold difference, the processing device 120A may generate a determination result that the predicted full MRI image of the target training sample does not satisfy the preset condition.

In 840, the processing device 120A (e.g., the model generation module 420) may determine, based on the determination result of each of the at least a portion of the at least one training sample (i.e., each target training sample), whether the intermediate subsampling model satisfies the termination condition.

In some embodiments, the target training sample(s) may include one target training sample. If the predicted full MRI image of the target training sample satisfies the preset condition, the processing device 120A may determine that the intermediate subsampling model satisfies the termination condition. If the predicted full MRI image of the target training sample does not satisfy the preset condition, the processing device 120A may determine that the intermediate subsampling model does not satisfy the termination condition.

In some embodiments, if the target training sample(s) include a plurality of target training samples, the processing device 120A may determine whether the intermediate subsampling model satisfies the termination condition based on the determination results of the target training samples. For example, the processing device 120A may determine the count of target training samples whose predicted full MRI image satisfies the preset condition. If the count exceeds a certain percentage (e.g., 60%, 70%, 80%, 90%, etc.) of the total count of the target training samples, the processing device 120A may determine that the intermediate subsampling model satisfies the termination condition. If the count does not exceed the certain percentage of the total count of the target training samples, the processing device 120A may determine that the intermediate subsampling model does not satisfy the termination condition.

It should be noted that the above description regarding the process 800 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. In some embodiments, whether the intermediate subsampling model satisfies the termination condition may be determined by another approach, for example, manually by a user.

Figure 9:
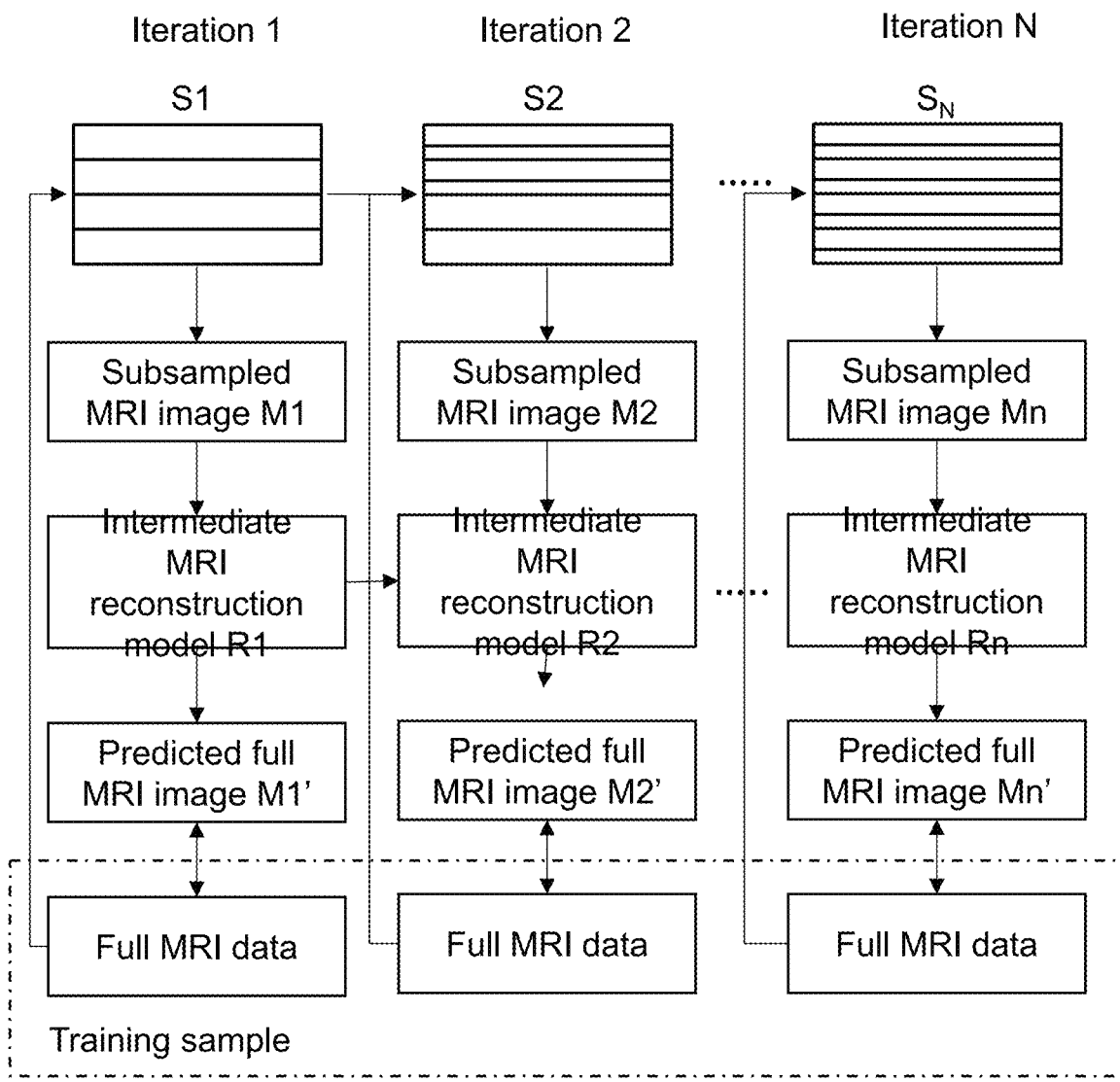
FIG. 9 is a schematic diagram illustrating an exemplary process for jointly training a preliminary subsampling model and a preliminary MRI reconstruction model according to some embodiments of the present disclosure.
Figure 10:
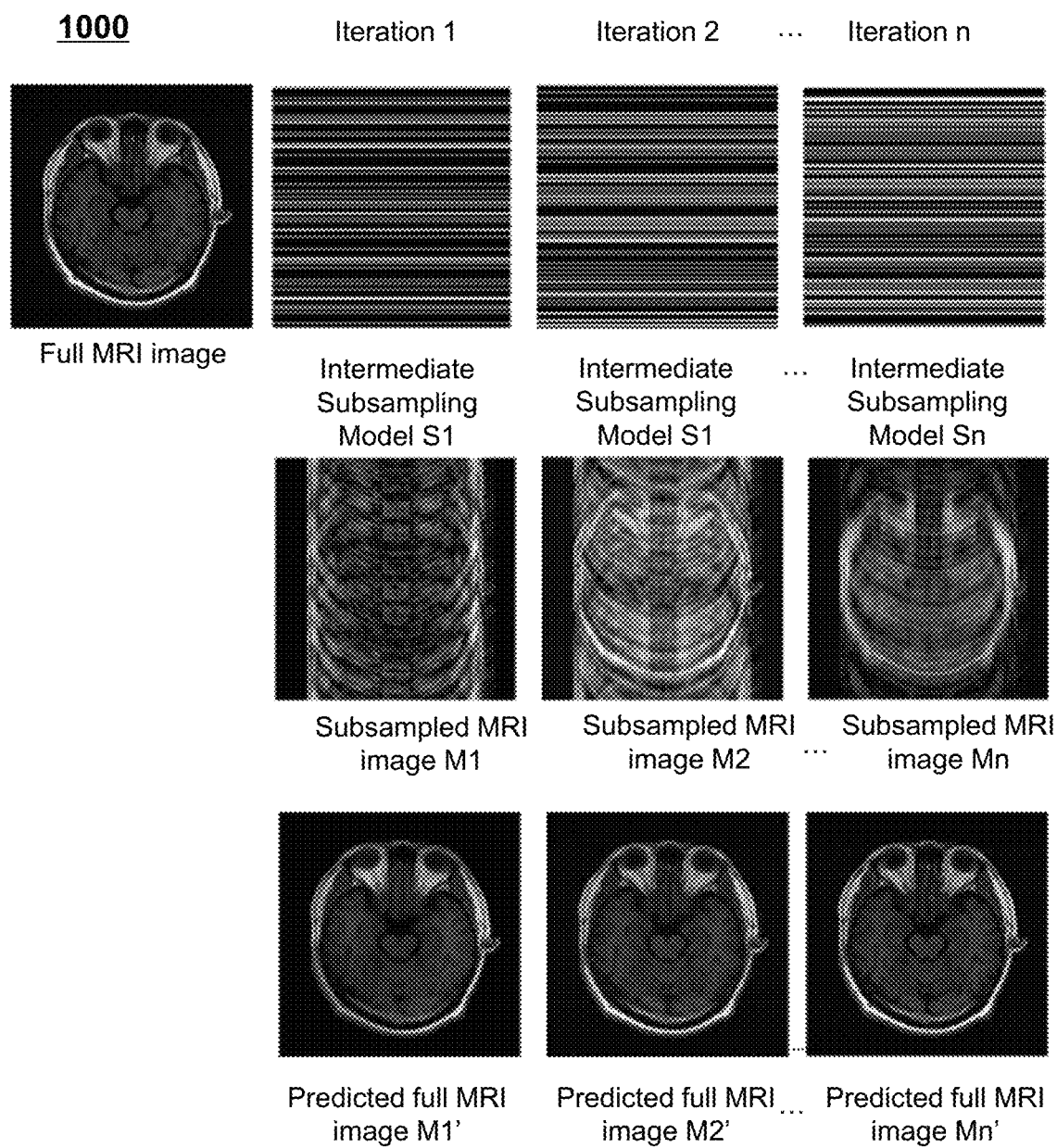
FIG. 10 is a schematic diagram illustrating exemplary intermediate subsampling models and images generated in process 900 according to some embodiments of the present disclosure.

FIG. 9 is a schematic diagram illustrating an exemplary process for jointly training a preliminary subsampling model and a preliminary MRI reconstruction model according to some embodiments of the present disclosure. FIG. 10 is a schematic diagram illustrating exemplary intermediate subsampling models and images generated in the process 900 according to some embodiments of the present disclosure. The process 900 may be an exemplary embodiment of the process 500 as described in FIG. 5.

As shown in FIGS. 9 and 10, the training process of the preliminary subsampling model and the preliminary MRI reconstruction model may include N iteration, wherein N may be any positive integer. Si represents an intermediate subsampling model of an $i^{th}$ iteration. Ri represents an intermediate MRI reconstruction model of the $i^{th}$ iteration. Mi represents a subsampled MRI image of a training sample generated in the $i^{th}$ iteration. Mi' represents a predicted full MRI image of a training sample generated in the $i^{th}$ iteration. Each training sample may include full MRI data, such as full k-space data and/or a full MRI image of a training subject. For illustration purposes, the following descriptions describe the training process of the preliminary subsampling model and the preliminary MRI reconstruction model based on one training sample (or referred to as a target training sample).

It should be noted that this is not intended to be limiting, and the training process may be implemented on a plurality of training samples.

In the first iteration (i.e., the iteration 1 in FIGS. 9 and 10), the intermediate subsampling model S1 may be the preliminary subsampling model as described in connection with operation 520. The intermediate MRI reconstruction model R1 may be the preliminary MRI reconstruction model as described in connection with operation 520. For a training sample, a subsampled MRI image M1 may be generated based on the intermediate subsampling model S1 and the full MRI data of the training sample. The subsampled MRI image M1 may be processed by an intermediate MRI reconstruction model R1 to generate a predicted full MRI image M1'.

Based on the predicted full MRI image M1' and the full MRI data of the training sample, whether the intermediate subsampling model S1 satisfies a termination condition may be determined. For example, a full MRI image of the training sample may be determined based on the full MRI data of the training sample. The predicted full MRI image M1' may be compared with the full MRI image to determine a difference between the predicted full MRI image M1' and the full MRI image. If the difference exceeds a threshold difference, it may be determined that the intermediate subsampling model S1 does not satisfy the termination condition. In response to determining that the intermediate subsampling model S1 does not satisfy the termination condition, the intermediate subsampling model S1 may be updated by performing 630 as described in connection with FIG. 6 to generate an intermediate subsampling model S2, and the intermediate MRI reconstruction model R1 may be updated by performing 640 as described in connection with FIG. 6 to generate an intermediate MRI reconstruction model R2.

In the second iteration (i.e., the iteration 2 in FIGS. 9 and 10), the intermediate subsampling model S2 may be the updated intermediate subsampling model S1 generated in the first iteration, and the intermediate MRI reconstruction model R2 may be the updated intermediate MRI reconstruction model R1 generated in the first iteration. The second iteration may be implemented in a similar manner as the first iteration, and the descriptions thereof are not repeated here. If it is determined the intermediate subsampling model S2 does not satisfy the termination condition, the intermediate subsampling model S2 and the intermediate MRI reconstruction model R2 may be further updated.

The training process may be terminated if the intermediate subsampling model in a certain iteration satisfies the termination condition. The intermediate subsampling model in the certain iteration may be designated as the subsampling model, and the intermediate MRI reconstruction model in the certain iteration may be designated as the MRI reconstruction model.

Referring to FIG. 10, in some embodiments, a training sample may include a full MRI image of the brain of a patient. The intermediate subsampling model Si of the $i^{th}$ iteration may define a plurality of k-space lines that need to be sampled. The subsampled MRI image Mi generated in the $i^{th}$ iteration may be an aliasing image. The subsampled MRI image Mi may be processed by an intermediate MRI reconstruction model of the $i^{th}$ iteration (not shown in FIG. 10) to generate a predicted full MRI image Mi', which is a non-aliasing image.

With the implementation of the training process, the count of k-space lines of the intermediate subsampling model in an iteration (S1–$S_N$ in FIG. 10) may be increased, the similarity between the generated subsampled MRI image of the iteration (M1–Mn in FIG. 10) and the full MRI image may be increased, and the similarity between the predicted full MRI image of the iteration (M1'–Mn' in FIG. 10) and the full MRI image may be increased. This suggests that during the training process, the accuracy of the preliminary subsampling model and the preliminary MRI reconstruction model may be gradually improved.

It should be noted that the above description regarding the process 900 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more operations of the process 900 described above may be omitted. As another example, the intermediate MRI reconstruction model Ri in the $i^{th}$ iteration (e.g., the first iteration, an iteration subsequent to the first iteration, etc.) may be the preliminary MRI reconstruction model. If it is determined that the intermediate subsampling model Si does not satisfy the termination condition in the $i^{th}$ iteration, only the intermediate subsampling model Si may be updated, and the training process may proceed to a next iteration without updating the intermediate MRI reconstruction model Ri. If it is determined that the intermediate subsampling model Si satisfies the termination condition in the $i^{th}$ iteration, the intermediate MRI reconstruction model Ri may be updated to generate the MRI reconstruction model.

In some embodiments, the processing device 120A may first update the model parameter(s) of the preliminary MRI reconstruction model to generate the MRI reconstruction model. Further, the processing device 120A may update the preliminary subsampling model based on the MRI reconstruction model and the at least one training sample. For example, the updating of the preliminary subsampling model may be performed in a similar manner as that as shown in FIG. 9, except that the intermediate MRI reconstruction model in each iteration may be replaced by the MRI reconstruction model and each iteration may be performed without updating the MRI reconstruction model.

In some embodiments, a plurality of MRI sequences may be performed on a subject to acquire different information of the subject. For example, an MRI sequence may be applied to the subject to generate a T1-weight image of the subject, and another MRI sequence may be applied to the subject to generate a T2-weight image of the subject. Exemplary MRI sequences may include a spin-echo (SE) sequence, an inversion recovery (IR) sequence, a gradient echo (GRE) sequence, an echo-planar imaging (EPI), a fast spin-echo (FSE) sequence, a fluid-attenuated inversion recovery (FLAIR) sequence, or the like, or a combination thereof.

In some embodiments, a universal subsampling model and/or a universal MRI reconstruction model may be generated for the plurality of MRI sequences. For example, a plurality of training samples, which include full MRI data acquired by the plurality of MRI sequences, may be used to generate the universal subsampling model and the universal MRI reconstruction model by performing the process 500 as described in connection with FIG. 5. In some embodiments, considering that different types of MRI sequences may have different characteristics (e.g., different pulse sequence parameters), a specific subsampling model and a specific MRI reconstruction model may be trained for each MRI sequence, in order to improve the accuracy of the generated subsampling models and the MRI reconstruction models of the MRI sequences.

Figure 11:
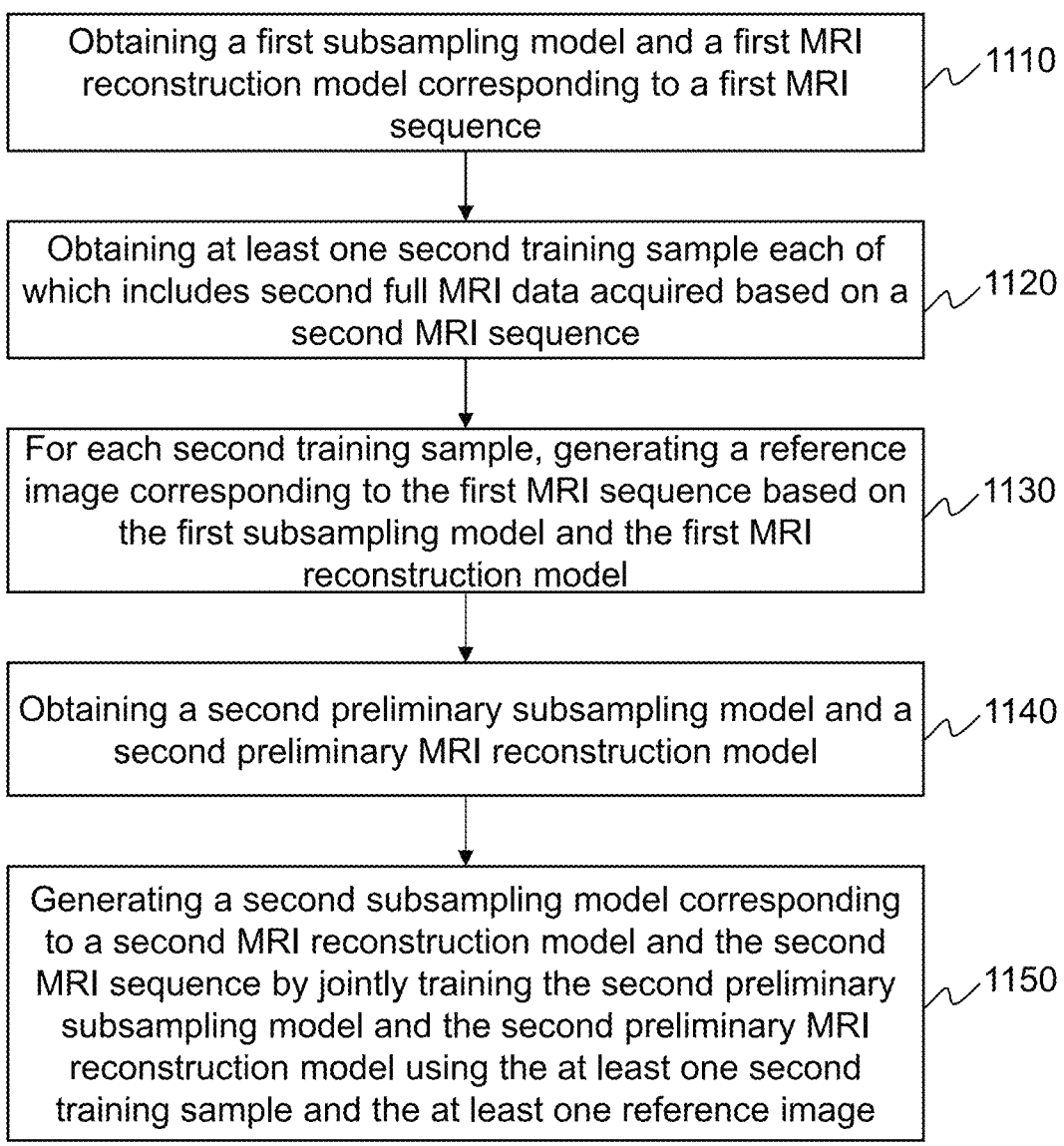
FIG. 11 is a flowchart of an exemplary process for generating subsampling models and MRI reconstruction models of a first MRI sequence and a second MRI sequence according to some embodiments of the present disclosure.

For illustration purposes, FIG. 11 illustrates is a flowchart of an exemplary process for generating subsampling models and MRI reconstruction models of a first MRI sequence and a second MRI sequence according to some embodiments of the present disclosure. The first MRI sequence and the second MRI sequence may be of different types.

In 1110, the processing device 120A (e.g., the model generation module 420) may obtain a first subsampling model (or referred to as a subsampling model) and a first MRI reconstruction model (or referred to as an MRI reconstruction model) corresponding to a first MRI sequence (or referred to as an MRI sequence).

In some embodiments, the processing device 120A may generate the first subsampling model and the first MRI reconstruction model based on at least one first training sample by performing process 500 as described in connection with FIG. 5. For example, the processing device 120A may obtain at least one first training sample each of which includes first full MRI data of a first training subject, wherein the first full MRI data may be acquired based on the first MRI sequence. The processing device 120A may further obtain a first preliminary subsampling model and a first preliminary MRI reconstruction model. The processing device 120A may also generate the first subsampling model and the first MRI reconstruction model by jointly training the first preliminary subsampling model and the first preliminary MRI reconstruction model using the at least one first training sample. The first subsampling model may be the trained first preliminary subsampling model, and the first MRI reconstruction model may be at least a portion of the trained first preliminary MRI reconstruction model.

As another example, the first subsampling model and the first MRI reconstruction model may be previously generated and stored in a storage device (e.g., the storage device 130, a storage device of the terminals(s) 140, or an external storage device). The processing device 120A may obtain the first subsampling model and the first MRI reconstruction model from the storage device.

In 1120, the processing device 120A (e.g., the model generation module 420) may obtain at least one second training sample each of which includes second full MRI data acquired based on a second MRI sequence.

In some embodiments, the second full MRI data of a second training sample may include second full k-space data and/or a second full MRI image of a second training subject. In some embodiments, a first training sample and a second training sample may include full MRI data of a same training subject or different training subjects. That is, the first training subject of a first training sample may be the same as or different from the second training subject of a second training sample. For example, a first training sample and a second training sample may include different sets of full MRI data of a same patient acquired using different MRI sequences.

In 1130, for each second training sample, the processing device 120A (e.g., the model generation module 420) may generate a reference image corresponding to the first MRI sequence based on the first subsampling model and the first MRI reconstruction model.

In some embodiments, for a second training sample, the processing device 120A may generate a second subsampled MRI image based on the first subsampling model and the second full MRI data of the second training sample. The processing device 120A may further generate the reference image by processing the second subsampled MRI image using the MRI reconstruction model. For example, the processing device 120A may obtain a second set of subsampled k-space data of the second training sample by applying the first subsampling model on the second full k-space data of the second training sample. Then, the second subsampled MRI image of the second training sample may be generated based on the second set of subsampled k-space data. Further, the processing device 120A may generate the second predicted full MRI image of the second training sample using the first MRI reconstruction model. The second predicted full MRI image of the second training sample may be designated as the reference image of the second training sample. In some embodiments, the generation of a second subsampled MRI image based on the second full MRI data of a second training sample and the first subsampling model may be performed in a similar manner as the generation of a subsampled MRI image based on full MRI data of a training sample and an intermediate subsampling model as described in connection with 810. The generation of the second predicted full MRI image of the second training sample based on the second subsampled MRI image and the first MRI reconstruction model may be performed in a similar manner as the generation of a predicted full MRI image of a training sample based on the subsampled MRI image and an intermediate MRI reconstruction model as described in connection with 820.

In some embodiments, the second training subject of a second training sample may be the same as the first training subject of a first training sample. In the last iteration of an iterative training process of the first subsampling model and the first MRI reconstruction model, a predicted full MRI image of the first training sample (e.g., the predicted full MRI image Mn' as shown in FIG. 9) may be generated. The predicted full MRI image of the first training sample generated in the last iteration may be obtained as the reference image of the second training sample.

In 1140, the processing device 120A (e.g., the obtaining module 410) may obtain a second preliminary subsampling model and a second preliminary MRI reconstruction model.

The second preliminary subsampling model may define a preliminary subsampling pattern corresponding to the second MRI sequence before model updating or training. In some embodiments, the obtaining of the second preliminary subsampling model may be performed in a similar manner as that of a preliminary subsampling model as described in connection with operation 520 in FIG. 5.

The second preliminary MRI reconstruction model refers to a preliminary algorithm or a preliminary model (e.g., a preliminary machine learning model) for MRI reconstruction corresponding to the second MRI sequence before model training or updating. In some embodiments, the second preliminary MRI reconstruction model may be of the same type as or a different type from the preliminary MRI reconstruction model as described in connection with operation 520. In some embodiments, the obtaining of the second preliminary MRI reconstruction model may be performed in a similar manner as that of a preliminary MRI reconstruction model as described in connection with operation 520.

In 1150, the processing device 120A (e.g., the model generation module 420) may generate a second subsampling model and a second MRI reconstruction model corresponding to the second MRI sequence by jointly training the second preliminary subsampling model and the second preliminary MRI reconstruction model using the at least one second training sample and the at least one reference image. The second subsampling model may be the trained second preliminary subsampling model, and the second MRI reconstruction model may be at least a portion of the trained second preliminary MRI reconstruction model.

In some embodiments, the training process of the second preliminary subsampling model and the second preliminary MRI reconstruction model (referred to as a second training process for the convenience of descriptions) may be performed in a similar manner as the training process of the preliminary subsampling model and the preliminary MRI reconstruction model as described in connection with operation 530, except that the reference image(s) generated in operation 1140 may be used in the second training process.

Figure 12:
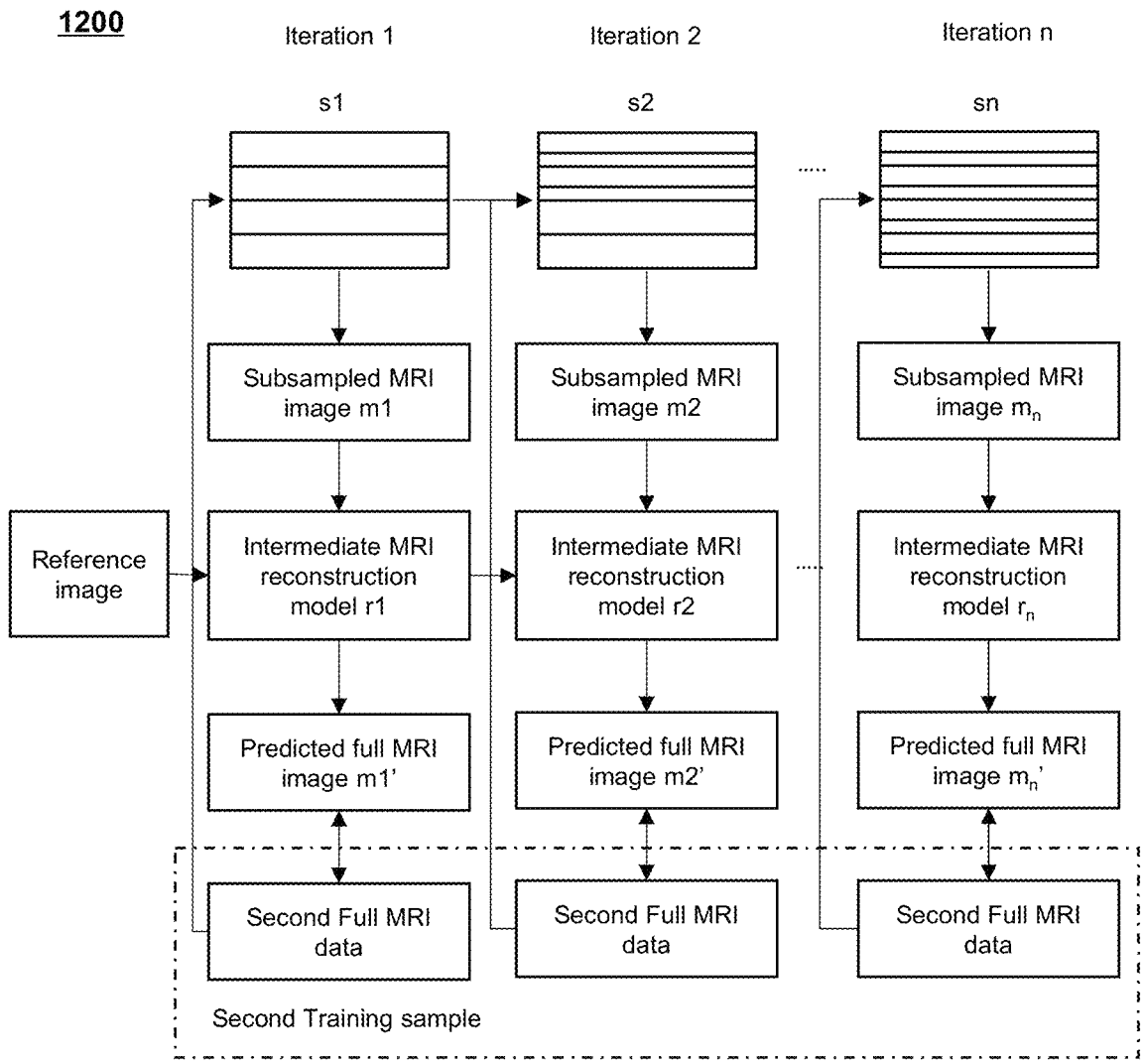
FIG. 12 is a schematic diagram illustrating an exemplary process for jointly training a second preliminary subsampling model and a second preliminary MRI reconstruction model corresponding to a second MRI sequence according to some embodiments of the present disclosure.

For illustration purposes, FIG. 12 illustrates a schematic diagram showing an exemplary process for jointly training the second preliminary subsampling model and the second preliminary MRI reconstruction model (i.e., the second training process) according to some embodiments of the present disclosure. One or more operations of process 1200 in FIG. 12 may be performed to achieve at least part of operation 1150.

As shown in FIG. 12, the second training process may include n iteration, wherein n may be any positive integer, and n may be the same as or different from N as described in connection with FIG. 9. In FIG. 12, $s_i$ represents an intermediate subsampling model of an $i^{th}$ iteration in the second training process; $r_i$ represents an intermediate MRI reconstruction model of the $i^{th}$ iteration; $m_i'$ represents a subsampled MRI image of a second training sample generated in the $i^{th}$ iteration; and $m_i'$ represents a predicted full MRI image of a second training sample generated in the $i^{th}$ iteration. Each second training sample may include second full MRI data, such as second full k-space data and/or a second full MRI image of a second training subject. For illustration purposes, the following descriptions describe the second training process based on one second training sample. It should be noted that this is not intended to be limiting, and the training process may be implemented on a plurality of second training samples.

In the first iteration (i.e., the iteration 1 in FIG. 12) of the second training process, the intermediate subsampling model s1 may be the second preliminary subsampling model as described in connection with operation 1140. The intermediate MRI reconstruction model r1 may be the second preliminary MRI reconstruction model as described in connection with operation 1140. For a second training sample, a subsampled MRI image m1 may be generated based on the intermediate subsampling model s1 and the second full MRI data of the second training sample. The subsampled MRI image s1 and a reference image of the second training sample may be processed by the intermediate MRI reconstruction model r1 to generate a predicted full MRI image m1'. In some embodiments, the intermediate MRI reconstruction model r1 may be a GAN model including a generator and a discriminator. The generator may be configured to transform the subsampled MRI image s1 and the reference image into non-aliasing images. The discriminator may be configured to determine whether an image is a second full MRI image or an image generated by the generator.

Based on the predicted full MRI image m1' and the second full MRI data, whether the intermediate subsampling model s1 satisfies a third termination condition may be determined. The third termination condition may be similar to the termination condition as described in connection with FIG. 9. The determination as to whether the intermediate subsampling model s1 satisfies the third termination condition may be performed in a similar manner as the determination as to whether the intermediate subsampling model S1 satisfies the termination condition as described in connection with FIG. 9. In response to determining that the intermediate subsampling model s1 does not satisfy the third termination condition, the intermediate subsampling model s1 may be updated to generate an intermediate subsampling model s2, and the intermediate MRI reconstruction model r1 may be updated to generate an intermediate MRI reconstruction model r2. The update of the intermediate subsampling model s1 and the intermediate MRI reconstruction model r1 may be performed in a similar manner as that of the intermediate subsampling model S1 and the intermediate MRI reconstruction model R1, respectively, as described in connection with FIG. 9.

In the second iteration (i.e., the iteration 2 in FIG. 12) of the second training process, the intermediate subsampling model s2 may be the updated intermediate subsampling model s1 generated in the first iteration of the second training process, and the intermediate MRI reconstruction model r2 may be the updated intermediate MRI reconstruction model r1 generated in the first iteration. The second iteration may be implemented in a similar manner as the first iteration, and the descriptions thereof are not repeated herein. If it is determined the intermediate subsampling model s2 does not satisfy the third termination condition, the intermediate subsampling model s2 and the intermediate MRI reconstruction model r2 may be further updated.

The second training process may be terminated if the intermediate subsampling model in a certain iteration satisfies the third termination condition. The intermediate subsampling model in the certain iteration of the second training process may be designated as the second subsampling model, and the intermediate MRI reconstruction model in the certain iteration may be designated as the second MRI reconstruction model.

Compared with the training process as described in connection with FIGS. 5 to 9, the second training process may be different in that in each iteration of the second training process, the predicted full MRI image of a second training sample may be determined based on the subsampled MRI image of the second training sample and also the reference image of the second training sample. The reference image may include structure information of the training subject of the second training sample acquired based on the first MRI sequence. The utilization of the reference image in the second training process may facilitate the reconstruction of the predicted full MRI image of the second training sample, and improve the training efficiency (e.g., by accelerating model convergence) and/or the training accuracy.

Figure 13:
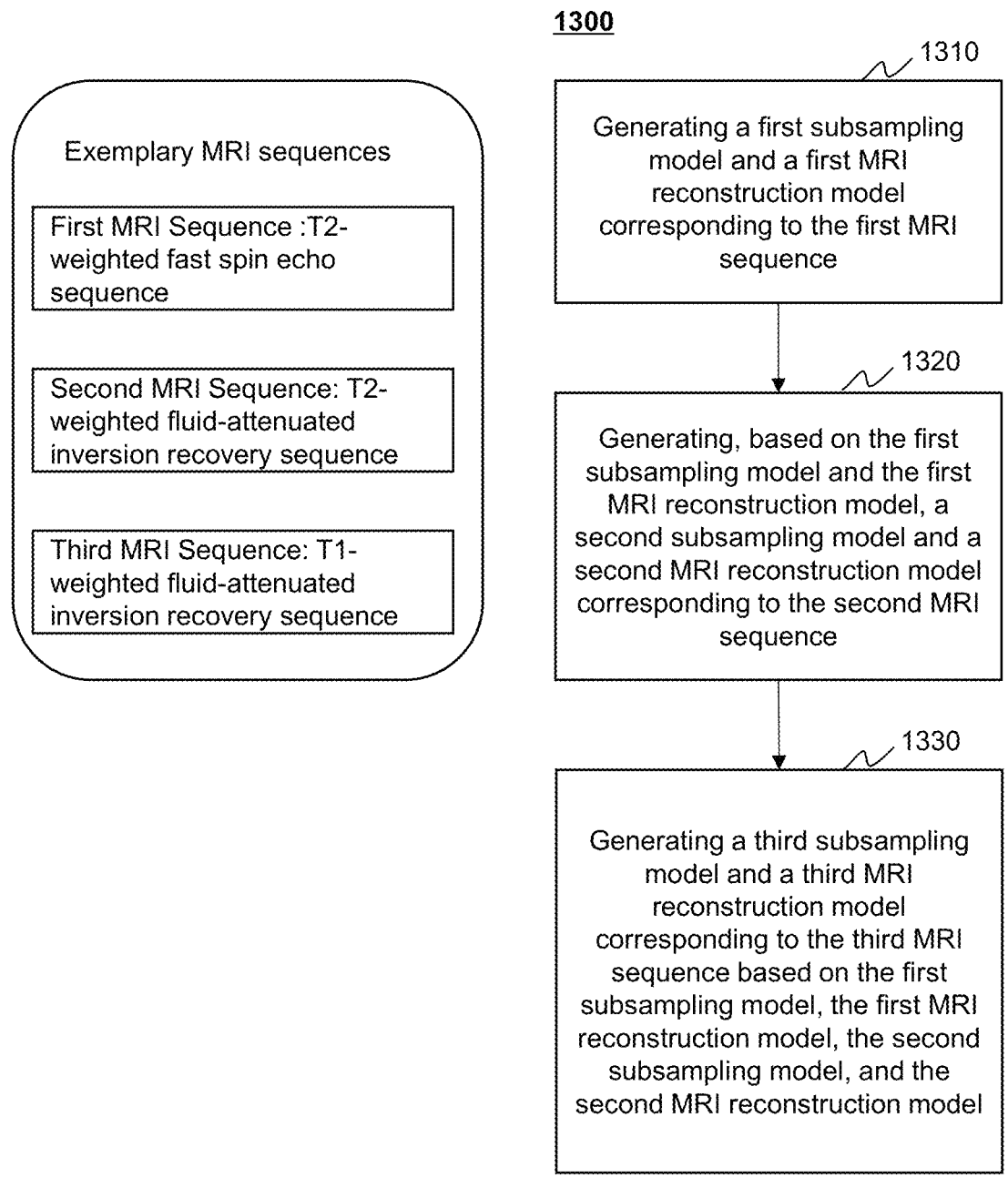
FIG. 13 illustrates an exemplary process for generating a subsampling model and an MRI reconstruction model for each of a first, a second, and a third MRI sequence according to some embodiments of the present disclosure.

In some embodiments, the processing device 120A may generate a subsampling model and an MRI reconstruction model for each of more than two MRI sequences. For illustration purposes, FIG. 13 illustrates an exemplary process for generating a subsampling model and an MRI reconstruction model for each of a first, a second, and a third MRI sequence according to some embodiments of the present disclosure. As shown in FIG. 13, the first MRI sequence may be a T2-weighted fast spin echo sequence, the second MRI sequence may be a T2-weighted fluid-attenuation inversion recovery sequence, and the third MRI sequence may be T1-weighted fluid-attenuation inversion recovery sequence. It should be noted that the first, second, and third MRI sequences provided in FIG. 13 are merely an example, and this is not intended to be limiting. Subsampling models and MRI reconstruction models corresponding to the three MRI sequences may be generated by performing process 1300 as shown in FIG. 13.

In 1310, the processing device 120A (e.g., the model generation module 420) may generate a first subsampling model and a first MRI reconstruction model corresponding to the first MRI sequence.

Operation 1310 may be performed in a similar manner as operation 1110 as described in connection with FIG. 11, and the descriptions thereof are not repeated here.

In 1320, the processing device 120A (e.g., the model generation module 420) may generate, based on the first subsampling model and the first MRI reconstruction model, a second subsampling model and a second MRI reconstruction model corresponding to the second MRI sequence.

In some embodiments, operation 1320 may be achieved by performing operations 1120 to 1150 as described in connection with FIG. 11.

In 1330, the processing device 120A (e.g., the model generation module 420) may generate a third subsampling model and a third MRI reconstruction model corresponding to the third MRI sequence based on the first subsampling model, the first MRI reconstruction model, the second subsampling model, and the second MRI reconstruction model.

For example, the processing device 120A may obtain at least one third training sample each of which includes third full MRI data of a third training subject acquired based on the third MRI sequence. For each of the at least one third training sample, the processing device 120A may generate a first reference image corresponding to the first MRI sequence and a second reference image corresponding to the second MRI sequence. The first reference image may be generated based on the first subsampling model and the first MRI reconstruction model, for example, in a similar manner as how the reference image of a second training sample is generated as described in connection with operation 1130. The second reference image may be generated based on the second subsampling model and the second MRI reconstruction model, for example, in a similar manner as how the reference image of a second training sample is generated as described in connection with operation 1130.

The processing device 120A may further generate the third subsampling model and the third MRI reconstruction model jointly training a third preliminary subsampling model and a third preliminary MRI reconstruction model using the at least one third training sample, the at least one first reference image, and the at least one second reference image. In some embodiments, the training process of the third preliminary subsampling model and the third preliminary MRI reconstruction model (also referred to as a third training process for brevity) may be performed in a similar manner as the second training process of the second preliminary subsampling model and the second preliminary MRI reconstruction model as described in connection with FIG. 12, except that in each iteration in the third training process, both the first reference image and the second reference image may be used to generate a predicted full MRI image of a third training sample.

It should be noted that the above descriptions regarding the process 1100, the process 1200, and the process 1300 are merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, one or more operations described above may be omitted and/or one or more additional operations may be added. As another example, the intermediate MRI reconstruction model $r_i$ in each iteration (e.g., the first iteration, an iteration subsequent to the first iteration, etc.) of the second training process may be the second preliminary MRI reconstruction model.

In some embodiments, the processing device 120A may generate the second subsampling model and the second MRI reconstruction model based on the at least one second training sample without utilizing the first subsampling model and the first MRI reconstruction model. For example, in the process 1100, operations 1110 and 1130 may be omitted, and operation 1150 may be performed in a similar manner as operation 530 as described in connection with FIG. 5. Similarly, the processing device 120A may generate the third subsampling model and the third MRI reconstruction model based on the at least one third training sample without utilizing the first subsampling model, the first MRI reconstruction model, the second subsampling model, and the second MRI reconstruction model.

FIG. 14 is a schematic diagram illustrating an exemplary process for generating a target full MRI image of a target subject according to some embodiments of the present disclosure. In some embodiments, process 1400 may be executed by the MRI system 100. For example, the process 1400 may be implemented as a set of instructions (e.g., an application) stored in a storage device (e.g., the storage device 130, the storage device 220, and/or the storage 390). In some embodiments, the processing device 120B (e.g., the processor 210 of the computing device 200, the CPU 340 of the mobile device 300, and/or one or more modules illustrated in FIG. 4A) may execute the set of instructions and may accordingly be directed to perform the process 1400.

In 1410, the processing device 120B (e.g., the obtaining module 430) may obtain target subsampled k-space data of a target subject by performing an MRI scan on the target subject according to a subsampling model.

As used herein, the target subject may include a biological subject and/or a non-biological subject to be imaged, such as a patient or a specific portion (e.g., an organ or a tissue) of the patient. The subsampling model may define how to perform subsampling during an MRI scan of a subject. During the MRI scan of the target subject, k-space data may be subsampled according to the subsampling model, and the subsampled k-space data may be designated as the target subsampled k-space data of the target subject.

In 1420, the processing device 120B (e.g., the image generation module 440) may generate a target subsampled MRI image of the target subject based on the target subsampled k-space data.

For example, the target subsampled MRI image may be generated based on the target subsampled k-space data by, for example, performing an inverse Fourier transformation on the target subsampled k-space data.

In 1430, the processing device 120B (e.g., the image generation module 440) may generate a target full MRI image of the target subject by processing the target subsampled MRI image using an MRI reconstruction model.

The MRI reconstruction model refers to an algorithm or a model (e.g., a machine-learning model) for MRI reconstruction. In some embodiments, the subsampling model and the MRI reconstruction model may be jointly generated by performing a process for generating a subsampling model corresponding to an MRI reconstruction model disclosed herein (e.g., the process 500 as described in connection with FIG. 5). Alternatively, the subsampling model and/or the MRI reconstruction model may be previously generated by a computing device (the processing device 120A or another processing device), and stored in a storage device (e.g., the storage device 130, a storage device of the terminals(s) 140, or an external storage device). The processing device 120B may retrieve the subsampling model and/or the MRI reconstruction model from the storage device.

In some embodiments, the processing device 120B may input the target subsampled MRI image into the MRI reconstruction model, or preprocess the target subsampled MRI image and input the preprocessed target subsampled MRI image into the MRI reconstruction model. The MRI reconstruction model may process its input and generate an output. The output of the MRI reconstruction model may include the target full MRI image or need to be post-processed to generate the target full MRI image.

In some embodiments, the MRI scan of the target subject may be implemented by one or more MRI sequences. Each of the one or more MRI sequences may correspond to a specific subsampling model and a specific MRI reconstruction model. The process 1400 may be performed for each MRI sequence to generate a target full MRI image corresponding to the MRI sequence. Merely by way of example, the target subject may be scanned by the first, second, and third MRI sequences sequentially as shown in FIG. 13. For the first MRI sequence, the processing device 120B may obtain a first set of target subsampled k-space data of the target subject according to the first subsampling model corresponding to the first MRI sequence. Then, the processing device 120B may generate a first target subsampled MRI image of the target subject based on the first set of target subsampled k-space data. The processing device 120B may further generate a first target full MRI image of the target subject by processing the first target subsampled MRI image using the first MRI reconstruction model corresponding to the first MRI sequence. Similarly, a second target full MRI image of the target subject may be generated based on the second subsampling model and the second MRI reconstruction model corresponding to the second MRI sequence; and a third target full MRI image of the target subject may be generated based on the third subsampling model and the third MRI reconstruction model corresponding to the third MRI sequence. By using a specific subsampling model and a specific MRI reconstruction model for each MRI sequence, the subsampling efficiency and/or accuracy may be improved, and the accuracy of the resulting target full MRI image(s) may be improved. In some embodiments, the first target full MRI image of the target subject may serve as a first target reference image, which may be used in the generation of the second target full MRI image of the target subject. The second target full MRI image of the target subject may serve and a second target reference image, and the first and second target reference images may be used in the generation of the third target full MRI image of the target subject.

It should be noted that the above description regarding the process 1400 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be added or omitted. For example, operation 1410 and operation 1420 may be combined into a single operation. As another example, one or more other optional operations (e.g., a storing operation for storing a processing result or an intermediate processing result) may be added in the process 1400.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

We claim:

1. A system for Magnetic Resonance Imaging (MRI), comprising:
at least one storage device including a set of instructions; and
at least one processor configured to communicate with the at least one storage device, wherein when executing the set of instructions, the at least one processor is configured to direct the system to perform operations including:
obtaining at least one training sample each of which includes full MRI data;
obtaining a preliminary subsampling model and a preliminary MRI reconstruction model; and
generating a subsampling model corresponding to an MRI reconstruction model by jointly training the preliminary subsampling model and the preliminary MRI reconstruction model using the at least one training sample, wherein the jointly training the preliminary subsampling model and the preliminary MRI reconstruction model includes updating the preliminary subsampling model in one or more iterations, wherein a first iteration includes:
for one of the at least one training sample,
generating a predicted full MRI image based on the training sample and the preliminary MRI reconstruction model;
generating predicted full MRI data based on the predicted full MRI image;
determining a plurality of k-space lines based on full MRI data of the training sample and the predicted full MRI data;
determining at least one difference between first data of the plurality of k-space lines corresponding to the full MRI data and second data of a plurality of k-space lines corresponding to the predicted full MRI data; and
updating the preliminary subsampling model based on a k-space line corresponding to a largest difference among the at least one difference.

2. The system of claim 1, wherein at least one iteration of the one or more iterations includes:
obtaining, based on the preliminary subsampling model and the preliminary MRI reconstruction model, an intermediate subsampling model and an intermediate MRI reconstruction model;
determining whether the intermediate subsampling model satisfies a termination condition; and
in response to determining that the intermediate subsampling model does not satisfy the termination condition, updating, based on the k-space line corresponding to the largest difference among the at least one difference, the intermediate subsampling model.

3. The system of claim 2, wherein the at least one iteration is the first iteration among the one or more iterations, the intermediate subsampling model is the preliminary subsampling model and the intermediate MRI reconstruction model is the preliminary MRI reconstruction model.

4. The system of claim 2, wherein
the one or more iterations include a plurality of iterations, the at least one iteration is subsequent to the first iteration among the one or more iterations,
the intermediate subsampling model is an updated intermediate subsampling model generated in a previous iteration, and
the intermediate MRI reconstruction model is an updated intermediate subsampling model generated in the previous iteration or the preliminary MRI reconstruction model.

5. The system of claim 2, wherein for the at least one iteration, the determining whether the intermediate subsampling model satisfies a termination condition comprises:
for each of the at least a portion of the at least one training sample,
generating, based on the intermediate subsampling model and the full MRI data of the training sample, a subsampled MRI image;
generating, based on the subsampled MRI image and the intermediate MRI reconstruction model, the predicted full MRI image; and
generating a determination result of whether the predicted full MRI image satisfies a preset condition; and
determining, based on the determination result of each of the at least a portion of the at least one training sample, whether the intermediate subsampling model satisfies the termination condition.

6. The system of claim 5, wherein for each of the at least a portion of the at least one training sample, the generating a determination result of whether the predicted full MRI image satisfies a preset condition comprises:
obtaining, based on the full MRI data of the training sample, a full MRI image;
determining a difference between the full MRI image and the predicted full MRI image of the training sample; and
determining whether the predicted full MRI image satisfies the preset condition by determining whether the difference exceeds a threshold difference.

7. The system of claim 5, wherein the determining at least one difference between first data of the plurality of k-space lines corresponding to the full MRI data and second data of a plurality of k-space lines corresponding to the predicted full MRI data comprises:
for each of the at least a portion of the at least one training sample,
obtaining the second data of the plurality of k-space lines corresponding to the predicted full MRI data by generating, based on the predicted full MRI image of the training sample, predicted full k-space data; and
obtaining the first data of the plurality of k-space lines corresponding to the full MRI data by obtaining, based on the full MRI data of the training sample, full k-space data.

8. The system of claim 7, wherein
the intermediate subsampling model defines a plurality of first k-space lines among the plurality of k-space lines, and
the determining at least one difference between first data of the plurality of k-space lines corresponding to the full MRI data and second data of a plurality of k-space lines corresponding to the predicted full MRI data comprises:
determining one or more second k-space lines by removing the plurality of first k-space lines from the plurality of k-space lines; and
for each of the one or more second k-space lines, determining a difference between the first data of the second k-space line and the second data of the second k-space line.

9. The system of claim 2, wherein in response to determining that the intermediate subsampling model does not satisfy the termination condition, the at least one iteration of the one or more iteration includes:
updating, based on the at least a portion of the at least one training sample, the intermediate MRI reconstruction model.

10. The system of claim 2, wherein the intermediate MRI reconstruction model is an updated intermediate subsampling model generated in a previous iteration,
in response to determining that the intermediate subsampling model satisfies the termination condition, the at least one iteration of the one or more iterations includes:
designating at least a portion of the intermediate subsampling model as the subsampling model; and
designating at least a portion of the intermediate MRI reconstruction model as the MRI reconstruction model.

11. The system of claim 2, wherein the intermediate MRI reconstruction model is the preliminary MRI reconstruction model, and
in response to determining that the intermediate subsampling model satisfies the termination condition, the at least one iteration of the one or more iterations further includes:
designating at least a portion of the intermediate subsampling model as the subsampling model; and
generating the MRI reconstruction model by updating the intermediate MRI reconstruction model based on the at least a portion of the at least one training sample.

12. The system of claim 1, wherein
the full MRI data of each of the at least one training sample is acquired based on a first MRI sequence, the subsampling model corresponds to the first MRI sequence, and
the at least one processor is further configured to direct the system to perform the operations including:
obtaining at least one second training sample each of which includes second full MRI data acquired based on a second MRI sequence;
for each of the at least one second training sample, generating a reference image corresponding to the first MRI sequence based on the subsampling model and the MRI reconstruction model;
obtaining a second preliminary subsampling model and a second preliminary MRI reconstruction model; and
generating a second subsampling model and a second MRI reconstruction model corresponding to the second MRI sequence by jointly training the second preliminary subsampling model and the second preliminary MRI reconstruction model using the at least one second training sample and the at least one reference image.

13. The system of claim 12, wherein for each of the at least one second training sample, the generating a reference image corresponding to the first MRI sequence based on the subsampling model and the MRI reconstruction model comprises:
generating, based on the subsampling model and the second full MRI data of the second training sample, a second subsampled MRI image; and
generating the reference image by processing the second subsampled MRI image using the MRI reconstruction model.

14. The system of claim 1, wherein the at least one processor is further configured to direct the system to perform the operations including:
obtaining target subsampled k-space data of a subject by performing an MRI scan on the subject according to the subsampling model;
generating a target subsampled MRI image of the subject based on the target subsampled k-space data; and
generating a target full MRI image of the subject by processing the target subsampled MRI image using the MRI reconstruction model.

15. The system of claim 1, wherein the MRI reconstruction model includes at least one of a convolution network or a generative adversarial network (GAN).

16. A system for Magnetic Resonance Imaging (MRI), comprising:
at least one storage device including a set of instructions; and
at least one processor configured to communicate with the at least one storage device, wherein when executing the set of instructions, the at least one processor is configured to direct the system to perform operations including:
obtaining target subsampled k-space data of a subject by performing an MRI scan on the subject according to a subsampling model corresponding to an MRI reconstruction model;
generating a target subsampled MRI image of the subject based on the target subsampled k-space data; and
generating a target full MRI image of the subject by processing the target subsampled MRI image using the MRI reconstruction model, wherein the subsampling model and the MRI reconstruction model are jointly trained using at least one training sample to update a preliminary subsampling model in one or more iterations, wherein a first iteration includes:

for one of the at least one training sample,
generating a predicted full MRI image based on the training sample and a preliminary MRI reconstruction model;
generating predicted full MRI data based on the predicted full MRI image;
determining a plurality of k-space lines based on full MRI data of the training sample and the predicted full MRI data;
determining at least one difference between first data of the plurality of k-space lines corresponding to the full MRI data and second data of a plurality of k-space lines corresponding to the predicted full MRI data; and
updating the preliminary subsampling model based on a k-space line corresponding to a largest difference among the at least one difference.

17. The system of claim 16, wherein the subsampling model includes at least a portion of the trained preliminary subsampling model, and
the MRI reconstruction model includes at least a portion of the trained preliminary MRI reconstruction model.

18. A method for Magnetic Resonance Imaging (MRI), the method being implemented on a computing device including at least one processor and at least one storage device, comprising:
obtaining at least one training sample each of which includes full MRI data;
obtaining a preliminary subsampling model and a preliminary MRI reconstruction model; and
generating a subsampling model corresponding to a n MRI reconstruction model by jointly training the preliminary subsampling model and the preliminary MRI reconstruction model using the at least one training sample, wherein the jointly training the preliminary subsampling model and the preliminary MRI reconstruction model includes updating the preliminary subsampling model in one or more iterations, wherein a first iteration includes:
for one of the at least one training sample,
generating a predicted full MRI image based on the training sample and the preliminary MRI reconstruction model;
generating predicted full MRI data based on the predicted full MRI image;
determining a plurality of k-space lines based on full MRI data of the training sample and the predicted full MRI data;
determining at least one difference between first data of the plurality of k-space lines corresponding to the full MRI data and second data of a plurality of k-space lines corresponding to the predicted full MRI data; and
updating the preliminary subsampling model based on a k-space line corresponding to a largest difference among the at least one difference.

19. The method of claim 18, wherein at least one iteration of the one or more iterations includes:
obtaining, based on the preliminary subsampling model and the preliminary MRI reconstruction model, an intermediate subsampling model and an intermediate MRI reconstruction model;
determining whether the intermediate subsampling model satisfies a termination condition; and
in response to determining that the intermediate subsampling model does not satisfy the termination condition, updating, based on the k-space line corresponding to the largest difference among the at least one difference, the intermediate subsampling model.

20. The method of claim 18, wherein
the full MRI data of each of the at least one training sample is acquired based on a first MRI sequence,
the subsampling model corresponds to the first MRI sequence, and
the method further includes:
obtaining at least one second training sample each of which includes second full MRI data acquired based on a second MRI sequence;
for each of the at least one second training sample, generating a reference image corresponding to the first MRI sequence based on the subsampling model and the MRI reconstruction model;
obtaining a second preliminary subsampling model and a second preliminary MRI reconstruction model; and
generating a second subsampling model and a second MRI reconstruction model corresponding to the second MRI sequence by jointly training the second preliminary subsampling model and the second preliminary MRI reconstruction model using the at least one second training sample and the at least one reference image.

* * * * *